US012409341B2

(12) United States Patent
Zhao et al.

(10) Patent No.: US 12,409,341 B2
(45) Date of Patent: Sep. 9, 2025

(54) METHODS AND SYSTEMS FOR DOSE DISTRIBUTION PREDICTION

(71) Applicant: SHANGHAI UNITED IMAGING HEALTHCARE CO., LTD., Shanghai (CN)

(72) Inventors: Kejun Zhao, Shanghai (CN); Runxin Liu, Shanghai (CN); Shuo Liu, Shanghai (CN); Binghuan Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 263 days.

(21) Appl. No.: 18/346,170

(22) Filed: Jun. 30, 2023

(65) Prior Publication Data

US 2024/0001149 A1 Jan. 4, 2024

(30) Foreign Application Priority Data

Jun. 30, 2022 (CN) .......................... 202210758229.6
Sep. 30, 2022 (CN) .......................... 202211207339.X

(51) Int. Cl.
*A61N 5/10* (2006.01)
*G16H 20/40* (2018.01)

(52) U.S. Cl.
CPC ......... *A61N 5/1038* (2013.01); *A61N 5/1039* (2013.01); *G16H 20/40* (2018.01)

(58) Field of Classification Search
CPC ...... A61N 5/10; A61N 5/1031; A61N 5/1038; A61N 5/1039; G16H 20/40
See application file for complete search history.

(56) References Cited

U.S. PATENT DOCUMENTS

2013/0197878 A1   8/2013   Fiege et al.
2017/0072221 A1   3/2017   Nord et al.
(Continued)

FOREIGN PATENT DOCUMENTS

CN   107441637 B   6/2019
CN   113941100 A   1/2022

OTHER PUBLICATIONS

Gyanendra Bohara et al., Using Deep Learning to Predict Beam-Tunable Pareto Optimal Dose Distribution for Intensity Modulated Radiation Therapy, Medical Physics, 2020, 42 pages.
(Continued)

*Primary Examiner* — Jurie Yun
(74) *Attorney, Agent, or Firm* — METIS IP LLC

(57) ABSTRACT

The present disclosure provides methods and systems for dose distribution prediction. The methods comprise obtaining historical state information and current state information of a target subject. The current state information may reflect the state of the target subject in a current treatment fraction, and the historical state information may reflect the state of the target subject prior to the current treatment fraction. The methods also comprise determining a feature parameter of at least one optimization target with respect to the current treatment fraction, and predicting a current dose distribution to be used in the current treatment fraction based on at least part of the historical state information, the current state information, and the feature parameter of the at least one optimization target using a dose prediction model, the dose prediction model being a trained machine learning model.

20 Claims, 13 Drawing Sheets

(56) References Cited

U.S. PATENT DOCUMENTS

2018/0178036 A1    6/2018    Laaksonen et al.
2020/0075148 A1    3/2020    Nguyen et al.
2022/0241611 A1    8/2022    Bokrantz et al.

OTHER PUBLICATIONS

Steven F. Petit et al., Increased Organ Sparing Using Shape-Based Treatment Plan Optimization for Intensity Modulated Radiation Therapy of Pancreatic Adenocarcinoma, Radiotherapy and Oncology, 102(1): 38-44, 2012.

Ma, Jianhui et al., A Feasibility Study on Deep Learning-Based Individualized 3D Dose Distribution Prediction, Medical Physics, 2021, 10 pages.

300

Obtaining historical state information and current state information of a target subject, the current state information reflecting the state of the target subject in a current treatment fraction, and the historical state information reflecting the state of the target subject prior to the current treatment fraction
310

↓

Determining at least one feature parameter of at least one optimization target with respect to the current treatment fraction
320

↓

Predicting a current dose distribution to be used in the current treatment fraction based on at least part of the historical state information, the current state information, and the at least one feature parameter of the at least one optimization target using a dose prediction model, the dose prediction model being a trained machine learning model
330

Obtaining a planning dose distribution, historical image data, and current image data of a target subject
410

Determining at least one feature parameter of at least one optimization target based on the planning dose distribution and the historical image data by using a first dose prediction model
420

Predicting a current dose distribution based on the current image data and the at least one feature parameter of the at least one optimization target by using the first dose prediction model
430

Obtaining current image data of a target subject, historical image data of the target subject, and at least one feature parameter of at least one optimization target with respect to a current treatment fraction
710

Predicting a current dose distribution to be used in the current treatment fraction based on the historical image data, the current image data, and the at least one feature parameter of the at least one optimization target using a second dose prediction model
720

Obtaining a plurality of second training samples, each of the plurality of second training samples includes sample historical image data, sample current image data, at least one sample feature parameter of at least one optimization target, and a sample dose distribution corresponding to a sample treatment fraction
901

Obtaining an output dose distribution by inputting the sample historical image data, the sample current image data, and the at least one sample feature parameter corresponding to the each second training sample into a third preliminary model
902

Determining one or more dose features based on the output dose distribution of each second training sample
903

Determining a value of a third loss function based on the does feature and the at least one sample feature parameter of the at least one optimization target of each second training sample
904

Determining a value of a fourth loss function based on the output dose distribution and the sample dose distribution of each second training sample
905

Obtaining a second dose prediction model by updating the third preliminary based on the value of the third loss function and the value of the fourth loss function
906

```
┌─────────────────────────────────────────────────────────┐
│  Obtaining historical image data and current image data │
│                   of a target subject                   │
│                         1010                            │
└─────────────────────────────────────────────────────────┘
                            │
                            ▼
┌─────────────────────────────────────────────────────────┐
│ For each of at least one target physical point in space,│
│ determining a first sampling point corresponding to the │
│ target physical point in the historical image data and  │
│ a second sampling point corresponding to the target     │
│ physical point in the current image data                │
│                         1020                            │
└─────────────────────────────────────────────────────────┘
                            │
                            ▼
┌─────────────────────────────────────────────────────────┐
│ For each of the at least one target physical point,     │
│ determining a position difference between a first       │
│ position of the first sampling point in the historical  │
│ image data and a second position of the second sampling │
│ point in the current image data                         │
│                         1030                            │
└─────────────────────────────────────────────────────────┘
                            │
                            ▼
┌─────────────────────────────────────────────────────────┐
│ Predicting a current dose distribution to be used in    │
│ the current treatment fraction based on the position    │
│ difference of each target physical point using a third  │
│ dose prediction model                                   │
│                         1040                            │
└─────────────────────────────────────────────────────────┘
```

Obtaining historical image data of a target subject, current image data of the target subject, and a planning dose distribution
1110

Determining, based on the current image data, a plurality of candidate dose distributions
1120

Determining, based on the historical image data and the planning dose distribution, a weight of each of the plurality of candidate dose distributions
1130

Predicting a current dose distribution to be used in the current treatment fraction based on the plurality of candidate dose distributions and their respective weights
1140

```
┌─────────────────────────────────────────────────────────┐
│ Obtaining a plurality of fourth training samples, each  │
│ fourth training sample including sample historical      │
│ image data, sample current image data, a sample        │
│ planning dose distribution, and a sample dose          │
│ distribution of a sample subject                        │
│ 1301                                                    │
└─────────────────────────────────────────────────────────┘
                            ↓
┌─────────────────────────────────────────────────────────┐
│ For each fourth training sample, inputting the sample   │
│ current image data of the fourth training sample into   │
│ initial expert models to determine a plurality of       │
│ intermediate dose distributions                         │
│ 1302                                                    │
└─────────────────────────────────────────────────────────┘
                            ↓
┌─────────────────────────────────────────────────────────┐
│ For each fourth training sample, inputting the sample   │
│ historical image data and the sample planning dose      │
│ distribution of the fourth training sample into an      │
│ initial gated model to determine an intermediate weight │
│ of each intermediate dose distribution                  │
│ 1303                                                    │
└─────────────────────────────────────────────────────────┘
                            ↓
┌─────────────────────────────────────────────────────────┐
│ For each fourth training sample, determining an output  │
│ dose distribution based on the intermediate dose        │
│ distributions and their respective intermediate weights │
│ 1304                                                    │
└─────────────────────────────────────────────────────────┘
                            ↓
┌─────────────────────────────────────────────────────────┐
│ Generating a fourth dose prediction model by updating   │
│ the initial expert models and the initial gated model   │
│ based on the output dose distribution and the sample    │
│ dose distribution of each fourth training sample        │
│ 1305                                                    │
└─────────────────────────────────────────────────────────┘
```

FIG. 13

METHODS AND SYSTEMS FOR DOSE DISTRIBUTION PREDICTION

CROSS-REFERENCE TO RELATED APPLICATIONS

This application claims priority to Chinese Patent Application No. 202210758229.6, filed on Jun. 30, 2022, and Chinese Patent Application No. 202211207339.X, filed on Sep. 30, 2022, the entire contents of each of which are hereby incorporated by reference.

TECHNICAL FIELD

The present disclosure generally relates to the field of medical technologies, and more particularly, relates to methods and systems for dose distribution prediction.

BACKGROUND

An adaptive radiotherapy is a new popular radiotherapy mode. Conventionally, before a radiotherapy treatment is performed on a patient (e.g., a cancer patient), a planning image (e.g., a computed tomography (CT) image, a magnetic resonance imaging (MRI) image) of the patient may be acquired. A treatment plan for the patient may be made based on the planning image. Following the treatment plan, a treatment may be delivered to the patient during several treatment fractions, spreading over a treatment period of multiple days (e.g., 2 to 5 weeks). However, during the treatment period, an anatomical change (e.g., weight loss or gain, growth, shrinkage, or disappearance of a tumor, the appearance of a new tumor, etc.) may take place within the body of the patient. The size and/or position of a certain organ may change between the planning and the time of a specific treatment fraction. Accordingly, before or during a current treatment fraction, current image data of the patient may be acquired and dose distribution to be used in the current treatment fraction needs to be determined based on the current image data.

Thus, it is desirable to provide methods and systems for dose distribution prediction, which is more accurate and efficient.

SUMMARY

An aspect of the present disclosure provides a method for dose distribution prediction implemented on a computing device having at least one processor and at least one storage device. the method comprises obtaining historical state information and current state information of a target subject. The current state information may reflect the state of the target subject in a current treatment fraction, and the historical state information may reflect the state of the target subject prior to the current treatment fraction. The method also comprises determining a feature parameter of at least one optimization target with respect to the current treatment fraction, and predicting a current dose distribution to be used in the current treatment fraction based on at least part of the historical state information, the current state information, and the feature parameter of the at least one optimization target using a dose prediction model, the dose prediction model being a trained machine learning model.

In some embodiments, the dose prediction model may include a first dose prediction model. The determining a feature parameter of at least one optimization target with respect to the current treatment fraction comprises obtaining planning dose distribution, and determining the feature parameter of the at least one optimization target based on the planning dose distribution and the historical state information by using the first dose prediction model. The current dose distribution may be determined using the first dose prediction model based on the current state information and the feature parameter.

In some embodiments, the first dose prediction model may include a first model and a second model. The first model is configured to determine the feature parameter of the at least one optimization target based on the planning dose distribution and the historical state information. The second model is configured to determine the current dose distribution based on the current state information and the feature parameter of the at least one optimization target.

In some embodiments, the historical state information may include historical image data of the target subject captured prior to the current treatment fraction. The determining feature parameter of the at least one optimization target based on the planning dose distribution and the historical state information by using the first dose prediction model comprises determining historical anatomical information of the target subject based on the historical image data; and determining the feature parameter of the at least one optimization target by inputting the historical anatomical information and the planning dose distribution into the first model. The current state information may include current image data of the target subject captured in the current treatment fraction. The predicting the current dose distribution based on the current state information and the feature parameter of the at least one optimization target by using the dose prediction model comprises determining current anatomical information of the target subject based on the current image data, and predicting the current dose distribution by inputting the current anatomical information and the feature parameter of the at least one optimization target into the second model.

In some embodiments, the obtaining the current dose distribution by inputting the current anatomical information and the feature parameter of the at least one optimization target into the second model comprises updating the feature parameter of the at least one optimization target based on a difference between the current anatomical information and the historical anatomical information, and obtaining the current dose distribution by inputting the current anatomical information and the one or more updated feature parameters of the at least one optimization target into the second model.

In some embodiments, the feature parameter of the at least one optimization target may include one or more Pareto optimization parameters of the at least one optimization target.

In some embodiments, a training process of the first dose prediction model comprises: obtaining a plurality of training samples, each of the plurality of training samples including first anatomical information and a first Pareto plane of a sample subject, the first Pareto plane including a plurality of first points, and each of the plurality of first points corresponding to first dose distribution and a first Pareto optimization parameter; for each of the plurality of first points of each of the plurality of training samples, obtaining a predicted Pareto optimization parameter by inputting the first anatomical information and the first dose distribution corresponding to the plurality of first points into a first preliminary model; and determining the first model by iteratively updating the first preliminary model based on the predicted Pareto optimization parameter and the first Pareto optimization parameter of the each of the plurality of first points.

In some embodiments, the each of the plurality of training samples further includes second anatomical information of the target subject, and the training process of the first dose prediction model further comprises: for the each of the plurality of training samples, determining, based on the first anatomical information and the first dose distribution of the training sample, a second Pareto optimization parameter by using the first model; generating a second Pareto plane based on the second anatomical information of the training sample, the second Pareto plane including a plurality of second points, and each of the plurality of second points corresponding to second dose distribution; and obtaining a predicted dose distribution by inputting the second anatomical information and the second Pareto optimization parameter into a second preliminary model; and obtaining the first dose prediction model by iteratively updating the second preliminary model based on the predicted dose distribution and the second dose distribution of the each of the plurality of training samples.

In some embodiments, the at least one optimization target may include at least one first optimization target whose feature parameter is set by a user and/or at least one second optimization target whose feature parameter is determined based on an original treatment plan.

In some embodiments, the feature parameter of the at least one optimization target may include a Dose Volume Histogram (DVH) curve of a target and/or an organ at risk (OAR) of the target subject.

In some embodiments, the dose prediction model may include a second dose prediction model. The second dose prediction model may include a plurality of layers. The historical state information and the current state information may be input into a first layer of the plurality of layers. The at least one optimization target may be input into a second layer of the plurality of layers.

Another aspect of the present disclosure provides a method for dose distribution prediction implemented on a computing device having at least one processor and at least one storage device. The method comprises obtaining historical image data and current image data of a target subject. The current image data may be captured before a current treatment fraction, and the historical image data may be captured prior to the current image data. For each of at least one target physical point in space, the method also comprises determining a first sampling point corresponding to the target physical point in the historical image data and a second sampling point corresponding to the target physical point in the current image data, and determining a position difference between a first position of the first sampling point in the historical image data and a second position of the second sampling point in the current image data. The method further comprises predicting a current dose distribution to be used in the current treatment fraction based on the position difference of each target physical point using a dose prediction model, the dose prediction model being a trained machine learning model.

In some embodiments, the first position of the first sampling point in the historical image data may include a first relative position of the first sampling point to a first OAR in the historical image data. The second position of the second sampling point in the current image data may include a second relative position of the second sampling point to a second OAR in the current image data. The position difference may include a difference between the first relative position and the second relative position.

In some embodiments, the first sampling point may be located within a first OAR in the historical image data. The first relative position may include a first distance between the first sampling point and a first target in the historical image data. The second sampling point may be located within a second OAR in the current image data. The second relative position may include a second distance between the second sampling point and a second target in the current image data. The position difference may include a difference between the first distance and the second distance.

In some embodiments, the first position of the first sampling point in the historical image data may include a third relative position of the first sampling point to a first target in the historical image data. The second position of the second sampling point in the current image data may include a fourth relative position of the second sampling point to a second target in the current image data. The position difference may include a difference between the third relative position and the fourth relative position.

In some embodiments, the determining a position difference between a first position of the first sampling point in the historical image data and a second position of the second sampling point in the current image data comprises for each of a plurality of beam eye view (BEV) planes, determining a first projection position of the first sampling point and a second projection position of the second sampling point on the BEV plane, determining a candidate difference between the first projection position and the second projection position, and determining the position difference between the first position and the second position based on the candidate differences corresponding to the plurality of BEV planes.

Another yet aspect of the present disclosure provides a method for dose distribution prediction implemented on a computing device having at least one processor and at least one storage device. The method comprises obtaining historical state information of a target subject, current state information of the target subject, and a planning dose distribution. The current state information may reflect the state of the target subject in a current treatment fraction, and the historical state information may reflect the state of the target subject prior to the current treatment fraction. The method also comprises determining a plurality of candidate dose distributions based on the current state information, determining a weight of each of the plurality of candidate dose distributions based on the historical state information and the planning dose distribution, and predicting a current dose distribution to be used in the current treatment fraction based on the plurality of candidate dose distributions and their respective weights.

In some embodiments, the plurality of candidate dose distributions may be determined using a plurality of expert models, each of which is configured to process the current state information and determine one of the plurality of candidate dose distributions.

In some embodiments, the plurality of expert models may be generated by jointly training a plurality of initial expert models. The plurality of initial experts models may have different initial model parameters.

In some embodiments, the plurality of expert models may be generated by separately training an initial expert model using different sets of training samples.

In some embodiments, the dose prediction model further may include a gated model, and the weight of each of the plurality of candidate dose distribution may be determined based on the historical state information and the planning dose distribution using the gated model.

In some embodiments, the gated model may be trained by performing a process including obtaining a plurality of training samples, each of which may include sample historical state information of a sample subject, a sample planning dose distribution corresponding to the sample historical state information, sample current state information of the sample subject, and a sample current dose distribution corresponding to the sample current state information. For each of the plurality of training samples, the process may also include determining a plurality of sample candidate dose distributions by processing the sample current state information of the training sample using the plurality of expert models, determining weights of the plurality of sample candidate dose distributions by processing the sample historical state information and the sample planning dose distribution of the training sample using an initial gated model, and determining a weighted dose distribution based on the plurality of sample candidate dose distributions and their weights. The process further may include determining the gated model by updating the initial gated model based on the weighted dose distribution and the sample current dose distribution of each of the plurality of training samples.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 3 is a flowchart illustrating an exemplary process for dose distribution prediction according to some embodiments of the present disclosure;

FIG. 4 is a flowchart illustrating an exemplary process for dose distribution prediction according to some embodiments of the present disclosure;

FIG. 7 is a flowchart illustrating an exemplary process 700 for dose distribution prediction according to some embodiments of the present disclosure;

FIG. 9A is a flowchart illustrating a training process of a second dose prediction model according to some embodiments of the present disclosure;

FIG. 10 is a flowchart illustrating an exemplary process for dose distribution prediction according to some embodiments of the present disclosure;

FIG. 11 is a flowchart illustrating an exemplary process for dose distribution prediction according to some embodiments of the present disclosure;

FIG. 13 is a flowchart illustrating a training process of a fourth dose prediction model according to some embodiments of the present disclosure.

DETAILED DESCRIPTION

Figure 1:
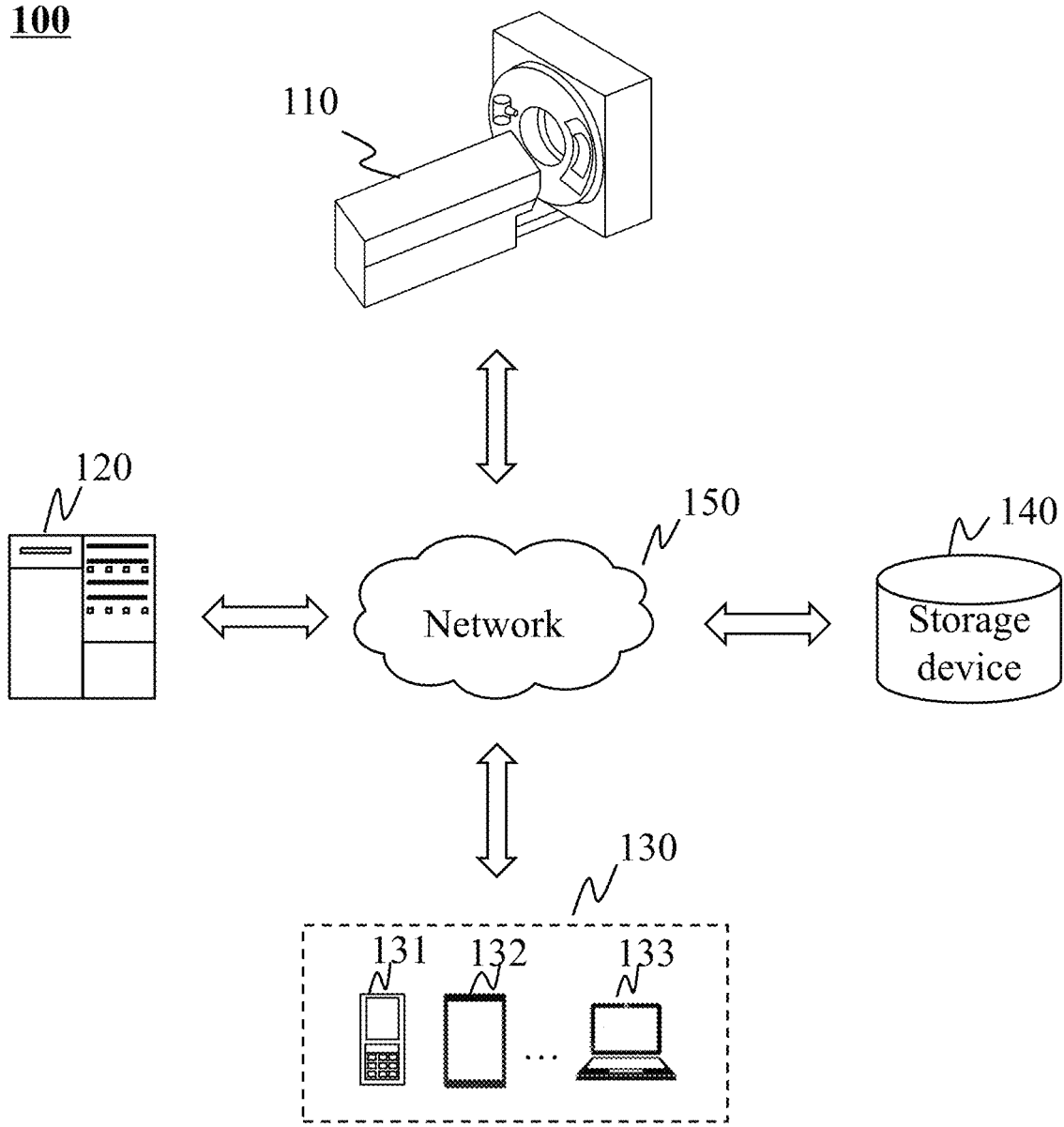
FIG. 1 is a schematic diagram illustrating an exemplary system for dose distribution prediction according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections or assembly of different levels in ascending order. However, the terms may be displaced by another expression if they achieve the same purpose.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The term "pixel" and "voxel" in the present disclosure are used interchangeably to refer to an element of an image. An anatomical structure shown in an image of a subject (e.g., a patient) may correspond to an actual anatomical structure existing in or on the subject's body. The term "object" and "subject" in the present disclosure are used interchangeably to refer to a biological object (e.g., a patient, an animal) or a non-biological object (e.g., a phantom). In some embodiments, the object may include a specific part, organ, and/or tissue of the object. For example, the object may include the head, the bladder, the brain, the neck, the torso, a shoulder, an arm, the thorax, the heart, the stomach, a blood vessel, soft tissue, a knee, a foot, or the like, or any combination thereof, of a patient.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale In the present disclosure, a representation of a subject (e.g., an object, a patient, or a portion thereof) in an image may be referred to as "subject" for brevity. For instance, a representation of an organ, tissue (e.g., a heart, a liver, a lung), or an ROI (e.g., a target, an OAR) in an image may be referred to as the organ, tissue, or ROI, for brevity. Further, an image including a representation of a subject, or a portion thereof, may be referred to as an image of the subject, or a portion thereof, or an image including the subject, or a portion thereof, for brevity. Still further, an operation performed on a representation of a subject, or a portion thereof, in an image may be referred to as an operation performed on the subject, or a portion thereof, for brevity. For instance, a segmentation of a portion of an image including a representation of an ROI from the image may be referred to as a segmentation of the ROI for brevity.

FIG. 1 is a schematic diagram illustrating an exemplary system 100 for dose distribution prediction (also referred to as a system 100) according to some embodiments of the present disclosure. In some embodiments, as illustrated in FIG. 1, a system 100 may include a radiotherapy device 110, a processing device 120, a terminal device 130, a storage device 140, and a network 150.

In some embodiments, the radiotherapy device 110 may include a therapy device. The therapy device may include a linear accelerator, a cyclotron, a synchrotron, or the like, which is configured to perform the radiotherapy on a treatment subject (also referred to as a target subject) through radiation. The therapy device may include an accelerator corresponding to different types of particles, such as photon, electron, proton, or heavy ion. The radiation used herein may include particle rays, photon rays, or the like. The particle rays may include neutron, proton, electron, μ meson, heavy ion, α-rays, or the like, or a combination thereof. The photon rays may include x-rays, γ-rays, ultraviolet, laser, or the like, or a combination thereof.

In some embodiments, the radiotherapy device 110 may further include a scanning device. The scanning device may be used to scan the target subject in a detecting region or a scanning region to obtain scan data of the target subject. In some embodiments, the target subject may include a biological subject and/or a non-biological subject. For example, the target subject may be living and/or nonliving organic and/or inorganic compounds.

In some embodiments, the scanning device may include a single-modality scanner and/or a multi-modality scanner. The single-modality scanner may include, for example, an ultrasonic scanner, an X-ray scanner, a Computed Tomography (CT) scanner, a Magnetic Resonance Imaging (MRI) scanner, an ultrasonic examination instrument, a Positron Emission Computed Tomography (PET) scanner, a Single-Photon Emission Computed Tomography (SPECT) scanner, an optical coherence tomography (OCT) scanner, an ultrasound (US) scanner, an intravascular ultrasound (IVUS) scanner, a near infrared spectroscopy (NIRS) scanner, a far infrared (FIR) scanner, or the like, or a combination thereof. The multi-modality scanner may include, for example, an X-ray imaging-MRI (X-ray-MRI) scanner, a PET-X-ray imaging (PET-X ray) scanner, a SPECT-MRI-X-ray imaging scanner, a PET-CT scanner, a SPECT-CT scanner, a Digital subtraction angiography-MRI (DSA-MRI) scanner, or the like, or a combination thereof. The scanners mentioned above are merely for illustration purposes, which is not limited to the scope of the present disclosure.

In some embodiments, the radiotherapy device 110 may include a treatment plan system (TPS), an image-guide radiotherapy (IGRT) device, or the like.

The processing device 120 may process data and/or information obtained from the radiotherapy device 110, the terminal device 130, the storage device 140, and/or other components of the system 100. For example, the processing device 120 may obtain current image data, historical image data, feature parameters of one or more optimization targets, candidate dose distributions, vital anatomical information, or the like, of the target subject from the terminal device 130 or the storage device 140 to process and analyze the data and/or the information illustrated herein. As another example, the processing device 120 may control a working of the radiotherapy device 110 based on the processing and analyzing result.

In some embodiments, the processing device 120 may be a single server or a server group. The server group may be centralized or distributed. In some embodiments, the processing device 120 may be local to or remote from the image processing system 100. For example, the processing device 120 may access information and/or data from the radiotherapy device 110, the terminal device 130, and/or the storage device 140 through the network 150. As another example, the processing device 120 may be connected to the radiotherapy device 110, the terminal device 130, and/or the storage device 140 directly to access the information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or any combination thereof.

In some embodiments, the processing device 120 may be integrated into the radiotherapy device 110. In some embodiments, the processing device 120 may be connected to the radiotherapy device 110 directly or indirectly to achieve a method and system illustrated in the present disclosure through a combined action.

The terminal device 130 may be connected to and/or in communication with the radiotherapy device 110, the processing device 120, and/or the storage device 140. In some embodiments, a user interaction may be achieved through the terminal device 130. In some embodiments, the terminal device 130 may include a mobile device 131, a tablet computer 132, a laptop computer 133, or the like, or any combination thereof. In some embodiments, the terminal device 130 (or a portion thereof) may be integrated in the processing device 120.

The storage device 140 may store data, instructions, and/or any other information. In some embodiments, the storage device 140 may store data (e.g., current image data, historical image data, candidate dose distributions, vital anatomical information, a feature parameter of an optimization target, etc.) obtained from the radiotherapy device 110, the processing device 120, and the terminal device 130. In some embodiments, the storage device 140 may store data and/or instructions that the processing device 120 may execute or use to perform exemplary methods described in the present disclosure.

In some embodiments, the storage device 140 may include one or more storage components. Each of the one or more storage components may be an independent device or a part of another device. In some embodiments, the storage device 140 may include a random-access memory (RAM), a read-only memory (ROM), a mass storage device, a removable storage device, a volatile read-and-write memory, or the like, or any combination thereof. In some embodiments, the p storage device 140 may be implemented on a cloud platform. In some embodiments, the storage device 140 may be part of the radiotherapy device 110, the processing device 120, or the terminal device 130.

The network 150 may include any suitable network that can facilitate the exchange of information and/or data. In some embodiments, at least one component (e.g., the radiotherapy device 110, the processing device 120, the terminal device 130, and the storage device 140) of the system 100 may communicate information and/or data with at least one another component of the system 100 via the network 150. For example, the processing device 120 may obtain a target image of the target subject from the radiotherapy device 110 via the network 150.

It should be noted that the above description of the system 100 is intended to be illustrative, and not to limit the scope of the present disclosure. Many alternatives, modifications, and variations will be apparent to those skilled in the art. For example, the system 100 may achieve similar or different functions on another device. However, these alternatives, modifications, and variations may not depart from the scope of the present disclosure.

Figure 2:
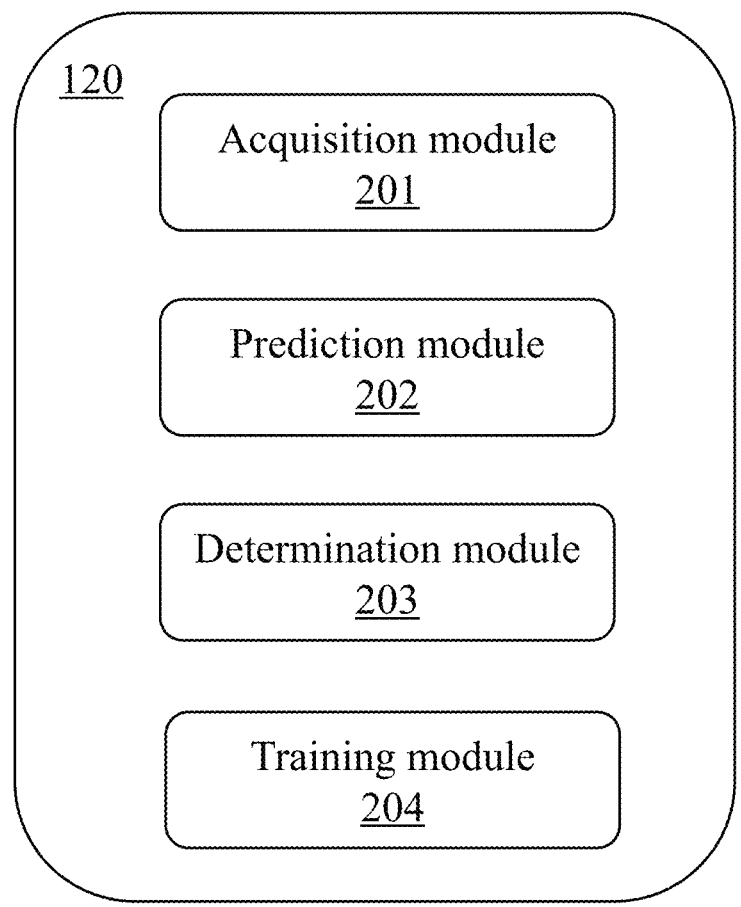
FIG. 2 is a block diagram illustrating an exemplary processing device according to some embodiments of the present disclosure.

FIG. 2 is a block diagram illustrating an exemplary processing device 120 according to some embodiments of the present disclosure. As illustrated in FIG. 2, the processing device 120 may include an acquisition module 201, a prediction module 202, a determination module 203, and a training module 204.

The acquisition module 201 may be configured to obtain related information of a target subject. In some embodiments, the acquisition module 201 may be configured to obtain historical state information and current state information of the target subject. The current state information may reflect the state of the target subject in a current treatment fraction, and the historical state information may reflect the state of the target subject prior to the current treatment fraction. In some embodiments, the acquisition module 201 may be configured to obtain a planning dose distribution, historical image data, current image data of the target subject, and/or a feature parameter of at least one optimization target. The at least one optimization target may also be referred to as a planning style feature, which may include a first optimization target and/or a second optimization. More descriptions regarding obtaining related information of a target subject may be found elsewhere in the present disclosure. See, e.g., operations 310, 410, 710, 1010, 1110, and relevant descriptions thereof.

The prediction module 202 may be configured to predict a current dose distribution to be used in the current treatment fraction based on at least part of the historical state information, the current state information, and the feature parameter of the at least one optimization target using a dose prediction model. The dose prediction model may be a trained machine learning model. In some embodiments, the prediction module 202 may be configured to predict the current dose distribution based on the current image data and the feature parameter of the at least one optimization target by using a first dose prediction model. In some embodiments, the prediction module 202 may be configured to predict the current dose distribution to be used in the current treatment fraction based on the historical image data, the current image data, and the feature parameter of the at least one optimization target using a second dose prediction model. In some embodiments, the prediction module 202 may be configured to predict the current dose distribution to be used in the current treatment fraction based on the position difference of each target physical point using a third dose prediction model. In some embodiments, the prediction module 202 may be configured to predict the current dose distribution to be used in the current treatment fraction based on a plurality of candidate dose distributions and their respective weights. More descriptions regarding predicting the current dose distribution to be used in the current treatment fraction may be found elsewhere in the present disclosure. See, e.g., operations 330, 430, 720, 1040, 1140, and relevant descriptions thereof.

The determination module 203 may be configured to determine a feature parameter of at least one optimization target with respect to the current treatment fraction. In some embodiments, the determination module 203 may be configured to determine a feature parameter of at least one optimization target based on the planning dose distribution and the historical image data by using the first dose prediction model. In some embodiments, the determination module 203 may be configured to determine a first sampling point corresponding to a target physical point in the historical image data and a second sampling point corresponding to the target physical point in the current image data. In some embodiments, the determination module 203 may be configured to determine a position difference between a first position of the first sampling point in the historical image data and a second position of the second sampling point in the current image data. In some embodiments, the determination module 203 may be configured to determine a plurality of candidate dose distributions based on the current image data. In some embodiments, the determination module 203 may be configured to determine a weight of each of the plurality of candidate dose distributions based on the historical image data and the planning dose distribution. More descriptions regarding the determination module 203 may be found elsewhere in the present disclosure. See, e.g., operations 320, 420, 1020, 1030, 1120, 1130, and relevant descriptions thereof.

The training module 204 may be configured to perform a training process to train a dose prediction model (e.g., a first dose prediction model, a second dose prediction model, a third dose prediction model, and a fourth dose prediction model). More descriptions regarding the training process may be found elsewhere in the present disclosure. See, e.g., FIGS. 5, 6, 9, 13, and relevant descriptions thereof.

It should be noted that the above description of the processing device 120 is intended to be illustrative, and not to limit the scope of the present disclosure. It should be understood that, for persons having ordinary skills in the art, each module may be combined arbitrarily, or form a subsystem to be connected with other modules under the teachings of the present disclosure. However, those variations and modifications do not depart from the scope of the present disclosure.

In some embodiments, the training module 204 and other modules described above may be implemented on different computing devices. Merely by way of example, the training module 204 may be implemented on a computing device of a vendor of the machine learning model(s) used for dose distribution prediction, while the other modules described above may be implemented on a computing device of a user of the machine learning model(s).

FIG. 3 is a flowchart illustrating an exemplary process 300 for dose distribution prediction according to some embodiments of the present disclosure. In some embodiments, the process 300 may be implemented by the processing device 120.

In 310, the processing device 120 (e.g., the acquisition module 201) may obtain historical state information and current state information of a target subject, the current state information reflecting the state of the target subject in a current treatment fraction, and the historical state information reflecting the state of the target subject prior to the current treatment fraction.

As used herein, state information may include any information that can reflect the state of the target subject. For example, the state information of the target subject may include a medical image of the subject and/or information determined based on the medical image (e.g., anatomical information). Merely by way of example, the historical state information may include historical image data (e.g., a historical image) of the target subject captured prior to the current treatment fraction, and the current state information may include current image data (e.g., a historical image) of the target subject captured in the current treatment fraction. For illustration purposes, the following descriptions take the historical image data as exemplary historical state information, and the current image data as exemplary current state information. It should be understood that this is not intended to be limiting, the terms "historical image data" and "historical image" hereinafter can be replaced by the term "historical state information," and the term "current image data" and "current image" hereinafter can be replaced by the term "current state information," unless the context clearly indicates otherwise.

A treatment process usually is performed in multiple treatment fractions or stages. In some embodiments, a planning image of the target subject (e.g., a tumor patient) may be obtained in a planning stage before the treatment process, and an original treatment plan for the multiple treatment fractions may be made in advance based on the planning image. The original treatment plan (e.g., the dose distribution) for a current treatment fraction may be adjusted based on current image data before the current treatment fraction. For example, an imaging of the target subject may be performed through a scanning device before the current treatment fraction, and the obtained image may be referred to as the current image data. The current image data may indicate a current condition of the target subject, such as a contour, size, structure, location, or the like, of a target region and/or organs at risk of the target subject. The current image data may be obtained through the radiotherapy device 110 (e.g., the scanning device of the radiotherapy device 110) or another scanning device. The historical image data may include a planning image corresponding to the original treatment plan or an image captured during one or more historical treatment fractions that have been performed.

In some embodiments, the historical image data and/or the current image data may be obtained from the storage device (e.g., the storage device 140 or an external storage device). Alternatively, the historical image data and/or the current image data may be obtained from the scanning device.

In some embodiments, the historical image data and/or the current image data may include a 2D image, a 3D image, a 4D image, or scan data corresponding to the images. In some embodiments, the historical image data and/or the current image data may include a single-modality image, such as an ultrasonic image, an X-ray image, a CT image, an MRI image, a PET image, a SPECT image, or the like. In some embodiments, the historical image data and/or the current image data may include a multi-modality image, such as a SPECT-MRI image, a PET-CT image, a SPECT-CT image, a CT-MRI image, or the like. A type of the historical image data and/or the current image data is not limited herein.

In some embodiments, the target subject may include a target region and organs at risk. The target region may be a target region where the radiotherapy is acted on, such as a lesion region. The organs at risk may be normal organs and/or tissues located around the lesion region. In some embodiments, the target region may be a gross tumor volume (GTV), a clinical target volume (CTV), or a planning target volume (PTV). The GTV may include a clinically malignant tissue (e.g., the tumor). The CTV may include the clinically malignant tissue (e.g., the GTV) and/or a subclinical malignant tissue at a certain probability level. The PTV may include the CTV and an additional margin surrounding the CTV (e.g., normal OARs near the CTV).

In 320, the processing device 120 (e.g., the determination module 203) may determine a feature parameter of at least one optimization target with respect to the current treatment fraction.

In some embodiments, the process of generating a treatment plan may be considered as a process of solving a multi-objective optimization problem that has a plurality of optimization targets, and the plurality of optimization targets may conflict with and/or constrain each other. For example, an optimization target of the treatment plan may be related to a dose feature. Exemplary dose features may include a cover ratio of the target region, an average dose received by the target region, a maximum dose received by the target region, a minimum dose received by the target region, a dose uniformity of the target region, a Dose Volume Histogram (DVH) curve of the target region, an average dose received by the organs at risk, a maximum dose received by the organs at risk, the organs at risk requiring a special protection (e.g., a maximum dose received by the organs at risk requiring a special protection is less than a threshold), a DVH curve of the organs at risk, a maximum dose per volume, or the like.

The feature parameter of the at least one optimization target may include one or more feature parameters of each optimization target. The feature parameter(s) of an optimization target may include, for example, a weight (indicating a significance of the optimization target) and a target value of the optimization target. For example, the optimization target may be related to the maximum dose of the target region, and a feature value of the optimization target may include a target value of the maximum dose of the target region, a weight of the optimization target that is related to the maximum dose of the target region, or the like.

In some embodiments, the feature parameter(s) of an optimization target may include a Pareto optimization parameter, such as coordinates of a point on a Pareto plane or a normal vector of a point on the Pareto plane. The Pareto plane may be used to solve a multi-objective optimization problem. The Pareto plane may be a multi-dimensional plane, and each dimension may correspond to an optimization target. A point (also referred to as a Pareto point) on the Pareto plane may correspond to a solution (i.e., a treatment plan, and each treatment plan includes a planning dose distribution) of the multi-objective optimization problem, and the solution may have a corresponding value of each optimization target. No better point that corresponds to a better value of each optimization target than the Pareto point can be found. The normal vector of the Pareto point may be a vector perpendicular to a tangent plane of the point, and the normal vector may be related to the weights of different optimization targets. The coordinates of the Pareto point may represent values of each optimization target of a corresponding solution, such as a dose of the target region of a corresponding treatment plan, an OAR dose, or the like. The solution corresponding to the Pareto point may be determined based on a dose optimization algorithm. An optimization target function (i.e., a weighted sum of each optimization target) may be determined when a weight of each optimization target corresponding to the Pareto point is determined. A corresponding treatment plan may be determined by solving the optimization target function based on feature information of the target subject and the dose optimization algorithm. Different Pareto optimization plans may be selected by selecting different points on the Pareto plane to find a better treatment plane and dose distribution.

In some embodiments, the at least one optimization target may include at least one first optimization target and/or at least one second optimization target. A feature value of the first optimization target may be set by a user. A feature value of the second optimization target may be determined based on the original treatment plan. More descriptions regarding the first optimization target and the second optimization target may be found elsewhere in the present disclosure. See, e.g., FIG. 7 and relevant descriptions thereof.

In some embodiments, a feature parameter of the at least one optimization target may include the DVH curve of the target region and/or the DVH curve of the organs at risk. A DVH curve may indicate a distribution of dose delivered to a unit volume in a region (e.g., the target region and the organs at risk). For example, an abscissa of the DVH curve may indicate a dose value delivered to a unit volume, and an ordinate of the DVH curve may indicate the number of unit volumes corresponding to the dose value. In some embodiments, one or more other feature parameters (e.g., the maximum dose of the target region, the OAR dose, etc.) may be determined based on the DVH curve of the target region and/or the DVH curve of the organs at risk.

In 330, the processing device 120 (e.g., the prediction module 202) may predict a current dose distribution to be used in the current treatment fraction based on at least part of the historical state information, the current state information, and the feature parameter of the at least one optimization target using a dose prediction model. The dose prediction model may be a trained machine learning model.

In the present disclosure, the dose distribution may indicate radiation dose to be delivered to different unit volumes of the target subject in the current treatment fraction. In some embodiments, the dose distribution may include a beam sub-field shape and a hop count. The beam sub-field shape may be a shape of the beam emitted from a certain angle during the treatment. The hop count may be a physical quantity used to measure treatment dose. In some embodiments, the current dose distribution may be represented as a 3D mesh. For example, a 3D image of the target subject may be divided into 100×100×100 grids, and a volume of each grid may be 3 mm×3 mm×3 mm. Each grid may be labeled as whether the grid belongs to a target region, organs at risk, normal tissues, or the like, and each grid may also have a label to indicate a corresponding radiation dose.

The dose prediction model may be a machine learning model used to predict the radiation dose. The dose prediction model may include but is not limited to a neural network model, a support vector machine model, a k-nearest neighbor model, a decision tree model, or the like, or any combination thereof. In some embodiments, the dose prediction model may include the neural network model. An exemplary neural network model may include Convolutional Neural Networks (CNN), Recurrent Neural Networks (RNN), Deep Neural Networks (DNN), Generative Adversarial Networks (GAN), U-net Networks, Res-net Networks, or the like.

In some embodiments, the dose prediction model may include a first dose prediction model. The first dose prediction model may be configured to determine the feature parameter of the optimization target(s) and also determine the current dose distribution. For example, the processing device 120 may obtain planning dose distribution, and determine the feature parameter based on the planning dose distribution and historical image data using the first dose prediction model. The processing device 120 may further determine the current dose distribution based on the current image data and the feature parameter using the first dose prediction model. More descriptions regarding the first dose prediction model may be found elsewhere in the present disclosure. See, e.g., FIG. 4 and relevant descriptions thereof.

In some embodiments, the optimization target(s) may include first optimization target(s) and/or second optimization target(s) as aforementioned. The dose prediction model may include a second dose prediction model. The processing device 120 may determine the current dose distribution by processing the current image data, the historical image data, and the feature parameter of the optimization target(s) using the second dose prediction model. More descriptions regarding the second dose prediction model may be found elsewhere in the present disclosure. See, e.g., FIGS. 7-9 and relevant descriptions thereof.

FIG. 4 is a flowchart illustrating an exemplary process 400 for dose distribution prediction according to some embodiments of the present disclosure. In some embodiments, the process 400 may be an embodiment of the process 300 as described in connection with FIG. 3.

In 410, the processing device 120 (e.g., the acquisition module 201) may obtain a planning dose distribution, historical image data, and current image data of a target subject.

More descriptions regarding the historical image data and the current image data may be found elsewhere in the present disclosure, which is not repeated herein. See, e.g., operation 310 and relevant descriptions thereof.

As described above, an original treatment plan of each treatment fraction may be determined during a treatment planning stage, which may include dose distribution planned to deliver during each treatment fraction. The planning dose distribution obtained in the operation 410 may be dose distribution corresponding to a specific treatment fraction in the original treatment plan. The specific treatment fraction may be the current treatment fraction or a historical treatment fraction that has been performed. In some embodiments, the original treatment plan or a dose distribution actually performed in the historical treatment fraction may be determined based on the historical image data (e.g., the historical image data may include a planning image). That is, the planning dose distribution may also be determined based on the historical image data. At this time, the planning dose distribution may be considered as being corresponding to the historical image data. For example, the planning dose distribution may include a dose value corresponding to each pixel point or each voxel point in the historical image data. As another example, the planning dose distribution may include the DVH curve of the target region and/or the DVH curve of the organs at risk in the historical image data.

In some embodiments, the processing device 120 may determine historical anatomical information of the target subject based on the historical image data, and determine current anatomical information of the target subject based on the current image data. The historical anatomical information and the current anatomical information may be used in subsequent dose prediction.

Anatomical information may indicate morphology information of the organs and/or tissues of the target subject. For example, the anatomical information may indicate the shape, edge, density, or the like, of the target region, the organs at risk, the normal organs, and/or the normal tissues. In some embodiments, the anatomical information may be represented through a medical image (e.g., a CT image, a PET image, an MR image, etc.). For example, a contour of the target region, the organs at risk, the normal organs, and/or the normal tissues may be sketched in the medical image, and the sketched image may be determined as the anatomical information. As another example, the target region and the organs at risk may be segmented from the medical image, and the segmented image may be determined as the anatomical information. In some embodiments, the anatomical information of the target subject may be changed during a treatment process. For example, a lesion (the target region) may become smaller during a treatment process, a poor appetite may cause the target subject to become thinner, or the like.

The historical anatomical information may be determined based on the historical image data, which may be original anatomical information of the target subject before the treatment or the anatomical information corresponding to the historical treatment fraction that has been performed. The current anatomical information may be determined based on the current image data, which may be the latest anatomical information of the target subject. For example, the current anatomical information may be the anatomical information of the upcoming current treatment fraction, the anatomical information of a certain period (e.g., prior one hour, prior two hours, prior five hours, prior one day, prior two days, prior one week, etc.) prior to the current treatment fraction, the real-time anatomical information during the current treatment fraction of the target subject, or the like.

For illustration purposes, the following may take the historical image data and the current image data as an example to describe a determination process of the current dose distribution. It should be understood that the historical anatomical information may replace the historical image data, and the current anatomical information may replace the current image data in the following descriptions.

In 420, the processing device 120 (e.g., the determination module 203) may determine a feature parameter of at least one optimization target based on the planning dose distribution and the historical image data by using a first dose prediction model.

In 430, the processing device 120 (e.g., the prediction module 202) may predict the current dose distribution based on the current image data and the feature parameter of the at least one optimization target by using the first dose prediction model.

In some embodiments, an input of the first dose prediction model may include the planning dose distribution, the historical image data, and the current image data. The first dose prediction model may determine the feature parameter of the at least one optimization target based on the planning dose distribution and the historical image data, and output the current dose distribution based on the current image data and the feature parameter of the at least one optimization target. In some embodiments, the input of the first dose prediction model may include the historical anatomical information corresponding to the historical image data and the current anatomical information corresponding to the current image data.

In some embodiments, the first dose prediction model may include a first model and a second model. An input of the first model may include the planning dose distribution and the historical image data, and an output of the first model may include the feature parameter of the at least one optimization target. An input of the second model may include the current image data and the feature parameter of the at least one optimization target output by the first model, and an output of the second model may include the current dose distribution. More descriptions regarding the first dose prediction model and a training method may be found elsewhere in the present disclosure. See, e.g., FIGS. 5 and 6 and relevant descriptions thereof.

Although the anatomical information of the same target subject may change during the treatment process, however, the at least one optimization target may be the same, thus, the feature parameter of the at least one optimization target may be substantially the same. A predicted feature parameter of the at least one optimization target may be obtained based on the historical image data and the planning dose distribution, and then the predicted feature parameter of the at least one optimization target may be applied to the treatment process of the current treatment fraction, so that a treatment effect that is substantially the same as the original treatment plan may be achieved.

In some embodiments, a posture of the target subject may change greatly under some conditions, which causes the feature parameter obtained based on the planning dose distribution to be not applicable to the current treatment. The processing device 120 may update the feature parameter based on a difference between the historical image data and the current image data. The processing device 120 may further determine the current dose distribution based on the current image data and the updated feature parameter. For example, the maximum dose (i.e., a target value corresponding to the optimization target) may become greater when a tumor of the target subject becomes bigger. Alternatively, if the tumor expands to a region close to a key organ, a weight corresponding to the maximum dose of the optimization target of a neighbor organ may be adjusted to be greater. The updated feature parameter may be more suitable to the target subject by updating the feature parameter based on the difference between the historical image data and the current image data, thereby improving an accuracy of the current dose distribution.

Figure 5:
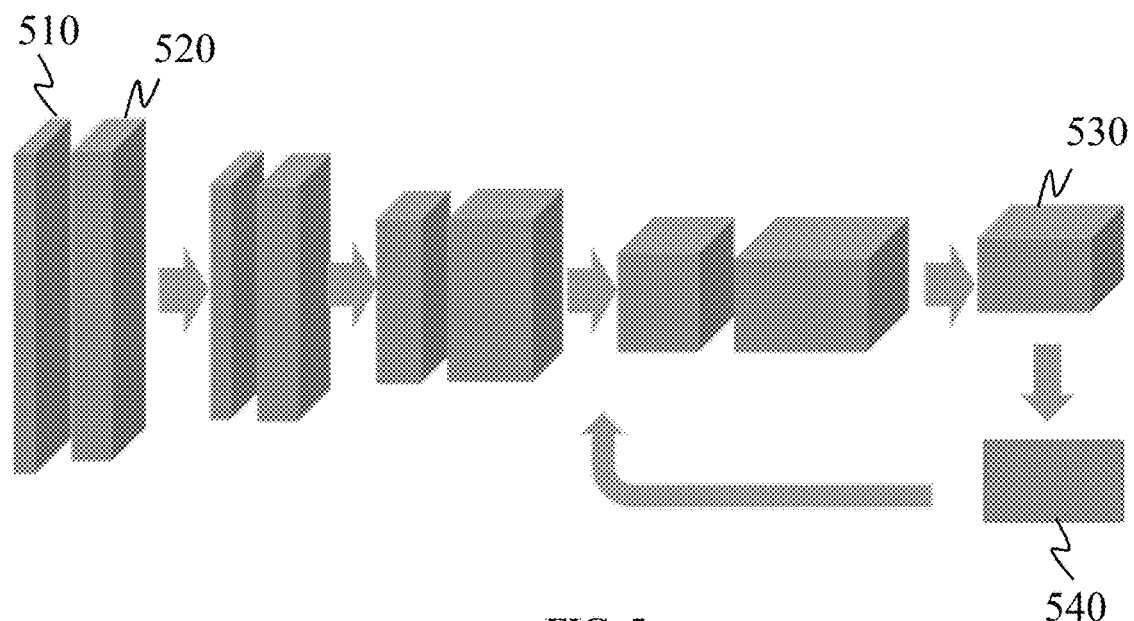
FIG. 5 is a schematic diagram illustrating a training process of a first model according to some embodiments of the present disclosure.

FIG. 5 is a schematic diagram illustrating a training process of a first model according to some embodiments of the present disclosure.

In some embodiments, a planning dose distribution and historical anatomical information may be input into the first model, and the first model may output a predicted feature parameter of at least one optimization target corresponding to the planning dose distribution and the historical anatomical information.

In some embodiments, the first model may include but is not limited to a neural network model, a support vector machine model, a k-nearest neighbor model, a decision tree model, or the like, or any combination thereof. In some embodiments, the first model may include a deep neural network model. In some embodiments, the first model may include at least one of the CNN, the Res-Net Networks, and the U-Net Networks.

In some embodiments, the first model may be obtained by training based on a plurality of first training samples and labels. For example, each first training sample may include first anatomical information and a first Pareto plane of a sample subject. The first Pareto plane may include a plurality of first points. Each first point may correspond to a solution to a dose optimization problem, which is also referred to as a first dose distribution. Each first point may also correspond to a first Pareto optimization parameter (i.e., the feature parameter), such as coordinates and/or a normal vector on the Pareto plane. The coordinates of the first point may indicate values of the plurality of optimization targets when the solution (i.e., the first dose distribution) corresponding to the point is used. In some embodiments, the first Pareto optimization parameter may be a training label, which may be set manually or automatically, or through other manners, which is not limited herein.

In some embodiments, the processing device 120 (e.g., the training module 204) may generate the first Pareto plane based on the first anatomical information. For example, the first Pareto plane may be generated based on the first anatomical information through a weighted sum method or ε constraint method. In some embodiments, the first dose distribution corresponding to each first point may be obtained from the first Pareto plane. For example, the first dose distribution corresponding to the point may be determined based on the first Pareto optimization parameter (i.e., the coordinates) corresponding to each point by determining the treatment plan based on the first Pareto optimization parameter.

In some embodiments, the processing device 120 may also obtain the first training samples from historical data. For example, anatomical information, a Pareto optimization parameter, and the corresponding dose distribution obtained from the historical data when the sample subject receives the historical treatment may be determined as the first anatomical information, the first Pareto optimization parameter, and the first dose distribution, respectively.

In some embodiments, during the training, the processing device 120 may input the first anatomical information corresponding to each first point and the first dose distribution into a first preliminary model to obtain a predicted Pareto optimization parameter (also referred to as a predicted parameter), and generate the first model by iteratively updating the first preliminary model based on the predicted parameter of each first point and the first Pareto optimization parameter.

For example, as illustrated in FIG. 5, first anatomical information 510 and a first dose distribution 520 may be input into the first preliminary model to obtain a predicted parameter 530, a value of a first loss function 540 may be determined based on the predicted parameter 530 and the first Pareto optimization parameter, and the first preliminary model may be updated based on the value of the first loss function 540. In some embodiments, the process illustrated above may be iteratively performed to update the first preliminary model until a specific condition is satisfied (e.g., the value of the first loss function 540 is less than a threshold). In some embodiments, during each iteration, one or more first training samples may be selected from a first training sample set, and the selection manner may be a random selection, a sequential selection, or the like. The first loss function 540 may be a Mean Square Error (MSE) loss function, a cross-entropy loss function, or the like, or any combination thereof.

Figure 6:
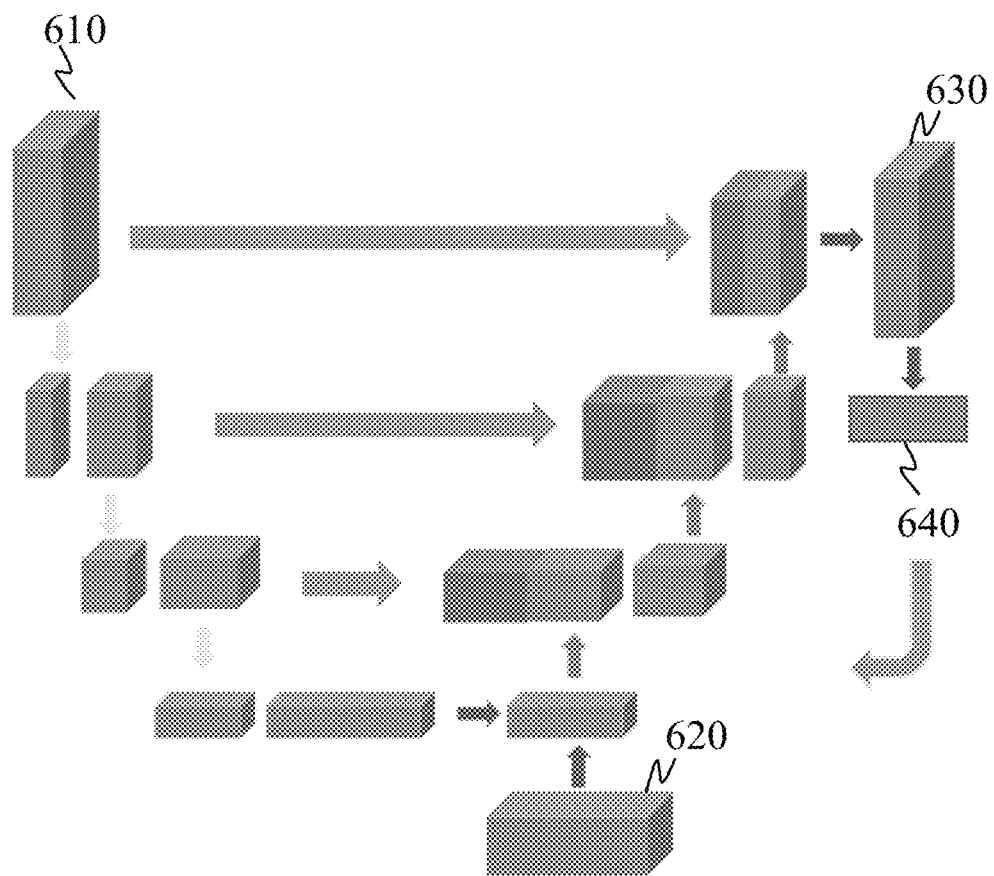
FIG. 6 is a schematic diagram illustrating a training process of a second model according to some embodiments of the present disclosure.

FIG. 6 is a schematic diagram illustrating a training process of a second model according to some embodiments of the present disclosure.

In some embodiments, the current anatomical information and the predicted Pareto optimization parameter may be input into the second model, and the second model may predict the current dose distribution corresponding to the current anatomical information.

In some embodiments, the second model may include but is not limited to a neural network model, a support vector machine model, a k-nearest neighbor model, a decision tree model, or the like, or any combination thereof. In some embodiments, the second model may include a deep neural network model. In some embodiments, the second model may include at least one of the CNN, the Res-Net Networks, and the U-Net Networks.

In some embodiments, each first training sample may further include second anatomical information of the sample subject. The first anatomical information and the second anatomical information of the sample subject may be the anatomical information corresponding to different times. For example, the first anatomical information of the sample subject may be considered as the historical anatomical information of the sample subject, and the second anatomical information may be considered as the current anatomical information of the sample subject.

In some embodiments, the processing device 120 may generate a second Pareto plane based on the second anatomical information. For example, the processing device 120 may generate the second Pareto plane based on the second anatomical information through a weighted sum method or ε constraint method. The second Pareto plane may include a plurality of second points, and each second point may correspond to a second solution of the dose optimization problem, which is also referred to as a second dose distribution. The second dose distribution may be a training label.

In some embodiments, the processing device 120 may input the first anatomical information and the first dose distribution into a trained first model to obtain a second Pareto optimization parameter. The processing device 120 may input the second anatomical information and the second Pareto optimization parameter into a second preliminary model to obtain a predicted dose distribution, determine a value of a second loss function based on the predicted dose distribution and a second dose distribution, and obtain the second model based on the value of the second loss function by iteratively updating the second preliminary model.

For example, as illustrated in FIG. 6, second anatomical information 610 and a second Pareto optimization parameter 620 may be input into the second preliminary model to obtain a predicted dose distribution 630, a value of a second loss function 640 may be determined based on the predicted dose distribution 630 and the second dose distribution, and the second preliminary model may be updated based on the value of the second loss function 640 to obtain the second model. The second loss function 640 may be a Mean Square Error (MSE) loss function, a cross-entropy loss function, or the like, or any combination thereof. In some embodiments, the processing device 120 may iteratively perform the process illustrated above to update the second preliminary model until a specific condition is satisfied.

It should be noted that the above description regarding FIG. 5 and FIG. 6 is merely provided for the purposes of illustration, and is not intended to limit the scope of the present disclosure. For example, the Pareto optimization parameter may be replaced by another feature parameter of the optimization target. As another example, the first anatomical information and the second anatomical information may be replaced by the historical image data and the current image data of the sample subject respectively.

In the embodiments of the present disclosure, a feature parameter of an optimization target may be determined based on planning dose distribution and historical image data to save a process of adjusting the feature parameter of the optimization target for a user, so that an automation degree of an adaptive radiotherapy mode may be higher. In some embodiments, a feature of the planning dose distribution may be preserved by predicting the current dose distribution based on the feature parameter determined based on the planning dose distribution and the historical image data to achieve a similar clinical effect to the planning dose distribution, thereby improving an accuracy of dose prediction. In addition, a time-consuming operation of generating a Pareto plane (e.g., the first Pareto plane and the second Pareto plane) may be changed from a dose prediction process to a model training process, thereby improving an efficiency of the dose prediction process.

FIG. 7 is a flowchart illustrating an exemplary process 700 for dose distribution prediction according to some embodiments of the present disclosure. In some embodiments, the process 700 may be an embodiment of the process 300 as described in connection with FIG. 3.

In 710, the processing device 120 (e.g., the acquisition module 201) may obtain current image data, historical image data, and feature parameter of at least one optimization target. The at least one optimization target may also be referred to as a planning style feature, which may include a first optimization target and/or a second optimization.

More descriptions about the historical image data and the current image data may be found elsewhere in the present disclosure. See, e.g., operation 310 and relevant descriptions thereof.

A feature parameter of a first optimization target may be set by a user (e.g., a doctor, the target subject), and the first optimization target is also referred to as an optimization target for a user tendency. For example, the feature parameter of the first optimization target may include a dose feature value that is tended to be achieved by a doctor, such as a cover ratio of the target region, an average dose received by the target region, a maximum dose received by the target region, a minimum dose received by the target region, a dose uniformity of the target region, an average dose received by the organs at risk, a maximum dose received by the organs at risk, the organs at risk requiring a special protection (e.g., a maximum dose received by the organs at risk requiring a special protection is less than a threshold), or the like. In some embodiments, the first optimization target may be a new dose requirement for the current treatment fraction proposed by the user. For example, if the target subject has a special requirement during the current treatment fraction, the user may propose the new dose requirement, such as reducing an average dose and/or a maximum dose of the radiation dose of the organs at risk or increasing the dose (e.g., an average dose, a maximum dose, a minimum dose, etc.) of the target region. A specific requirement of the user for the current treatment fraction may be better satisfied by considering the first optimization target, so that the normal organs and/or tissues around a tumor may be better protected. In some embodiments, the feature parameter of the first optimization target may be input by the user through an operation interface (e.g., an operation interface of the processing device 120 or the terminal device 130).

A feature parameter of the second optimization target may be determined based on an original treatment plan. In some embodiments, the original treatment plan may be a treatment plan generated based on a planning image captured in a planning stage. For example, the original treatment plan may include a treatment plan corresponding to the current treatment fraction or a historical treatment fraction, and the feature parameter of the second optimization target may be determined based on the treatment plan. For example, the feature parameter of the second optimization target may include a dose feature value determined based on the original treatment plan, such as a planning dose distribution, a cover ratio of the target region, an average dose received by the target region, a maximum dose received by the target region, a minimum dose received by the target region, a dose uniformity of the target region, an average dose received by the organs at risk, a maximum dose received by the organs at risk, or the like. In some embodiments, the original treatment plan may also be a treatment plan determined before the current treatment fraction (e.g., during a historical treatment fraction). By considering the second optimization target, the original treatment plan may provide efficient reference information, so that the planning style may be kept, and the determined current dose distribution may be better fitted with the planning style to adapt to individual case differences.

In some embodiments, the feature parameter of an optimization target (e.g., a first or second optimization target) may include the DVH curve of the target region of the target subject and/or the DVH curve of the organs at risk. The DVH curve of the target region and/or the DVH curve of the organs at risk may indicate a specific dose requirement for the target region and/or the organs at risk. For example, the DVH curve of the target region and/or the DVH curve of the organs at risk set by the doctor may be determined as the feature parameter of the first optimization target. As another example, the DVH curve of the target region and/or the DVH curve of the organs at risk determined based on the original treatment plan may be determined as the feature parameter of the second optimization target.

In 720, the processing device 120 (e.g., the prediction module 202) may predict the current dose distribution to be used in the current treatment fraction based on the historical image data, the current image data, and the feature parameter of the at least one optimization target using a second dose prediction model.

Figure 8:
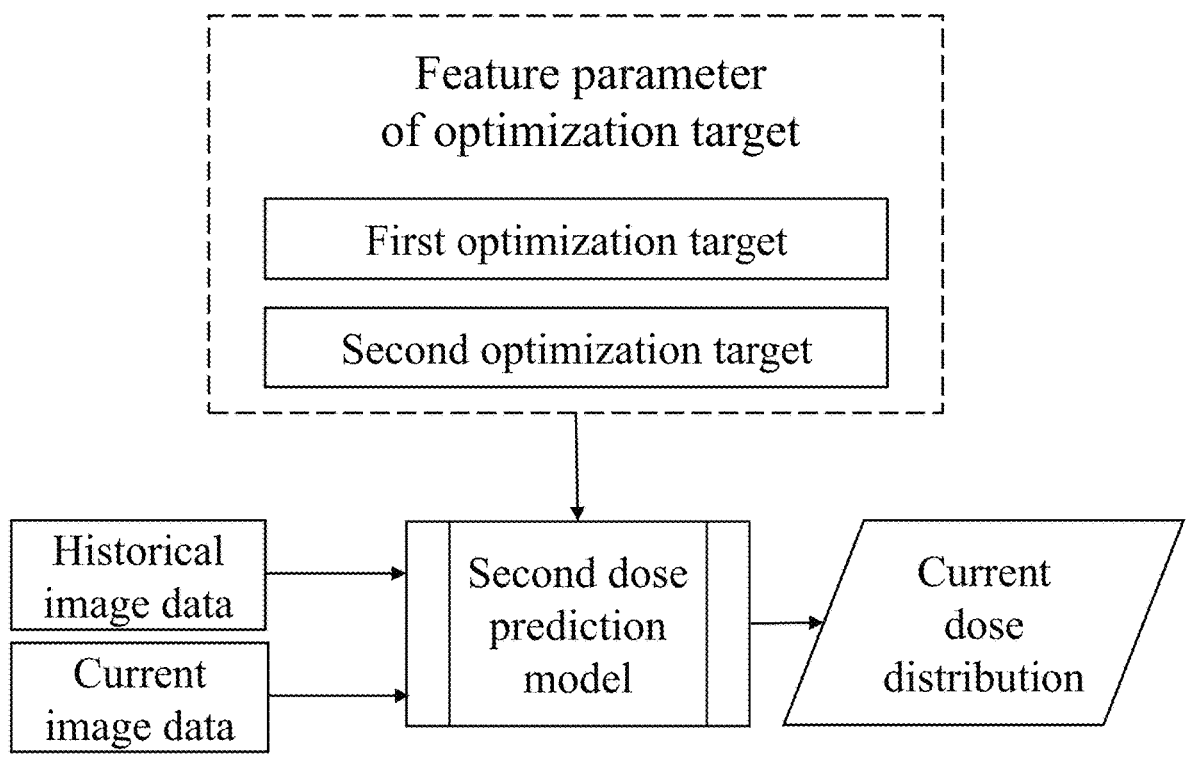
FIG. 8 is a schematic diagram illustrating an exemplary second dose prediction model according to some embodiments of the present disclosure.

As illustrated in FIG. 8, the input of the second dose prediction model may include the current image data, the historical image data, and the feature parameter of the at least one optimization target (the feature parameter of the first optimization target and the feature parameter of the second optimization target), and the output of the second dose prediction model may include the predicted current dose distribution corresponding to the current image data. In some embodiments, a difference between the current anatomical information corresponding to the current image data and the historical anatomical information corresponding to the historical image data may be determined, and the difference may be input into the second dose prediction model. For example, the current anatomical information may include a sketched result of a region of interest (e.g., the target region and the organs at risk) in the current image data, and the historical anatomical information may include a sketched result of a region of interest (e.g., the target region and the organs at risk) in the historical image data. In some embodiments, the current anatomical information corresponding to the current image data and the historical anatomical information corresponding to the historical image data may be input into the second dose prediction model, and the second dose prediction model may determine the difference of the anatomical information automatically. In some embodiments, the current image data and the historical image data may be input into the second dose prediction model directly, and the second dose prediction model may determine the current anatomical information, the historical anatomical information, and the difference between the current anatomical information and the historical anatomical information automatically.

In some embodiments, the feature parameter of the at least one optimization target may be transformed into a feature vector that is able to be recognized by the second dose prediction model, and the feature vector may be input into the second dose prediction model. In some embodiments, the feature parameter of the at least one optimization target may be input into the second dose prediction model directly, and the second dose prediction model may extract a needed feature based on the feature parameter of the at least one optimization target. For example, the DVH curve of the target region and/or the DVH curve of the organs at risk may be input into the second dose prediction model, and the second dose prediction model may extract the feature parameter of the first optimization target and/or the second optimization target automatically, such as a planning dose distribution, a cover ratio of the target region, an average dose received by the target region, a maximum dose received by the target region, a minimum dose received by the target region, a dose uniformity of the target region, an average dose received by the organs at risk, a maximum dose received by the organs at risk, the organs at risk requiring a special protection, or the like.

FIG. 9A is a flowchart illustrating a training process 900 of a second dose prediction model according to some embodiments of the present disclosure. In some embodiments, the process 900 may be performed by the training module 204.

In 901, the processing device 120 may obtain a plurality of second training samples. Each of the plurality of second training samples may include sample historical image data, sample current image data, a sample feature parameter of at least one optimization target, and a sample dose distribution corresponding to a sample treatment fraction. The sample dose distribution may be determined as a training label.

In some embodiments, the processing device 120 may determine the second training samples based on historical data. For example, historical image data, current image data, a feature parameter of an optimization target, and a corresponding dose distribution of a performed treatment fraction of the sample subject may be obtained from the historical data. In some embodiments, the sample dose distribution may be the dose distribution performed on the sample subject during the sample treatment fraction, and the sample dose distribution may correspond to the current image data of the sample treatment fraction. The sample dose distribution may be set in a manual manner or an automatic manner, or by another manner, which is not limited herein.

In some embodiments, the processing device 120 may obtain the second dose prediction model by using the second training samples to train a third preliminary model.

In 902, the processing device 120 may obtain an output dose distribution by inputting the sample historical image data, the sample current image data, and the sample feature parameter corresponding to each second training sample into the third preliminary model.

In 903, the processing device 120 may determine one or more dose features based on the output dose distribution of each second training sample.

In some embodiments, the processing device 120 may determine the dose distribution, a cover ratio of the target region, an average dose received by the target region, a maximum dose received by the target region, a minimum dose received by the target region, a dose uniformity of the target region, an average dose received by the organs at risk, a maximum dose received by the organs at risk, the organs at risk requiring a special protection, or the like, based on the output dose distribution.

In 904, the processing device 120 may determine a value of a third loss function based on the does feature and the sample feature parameter of the at least one optimization target of each second training sample.

Figure 9B:
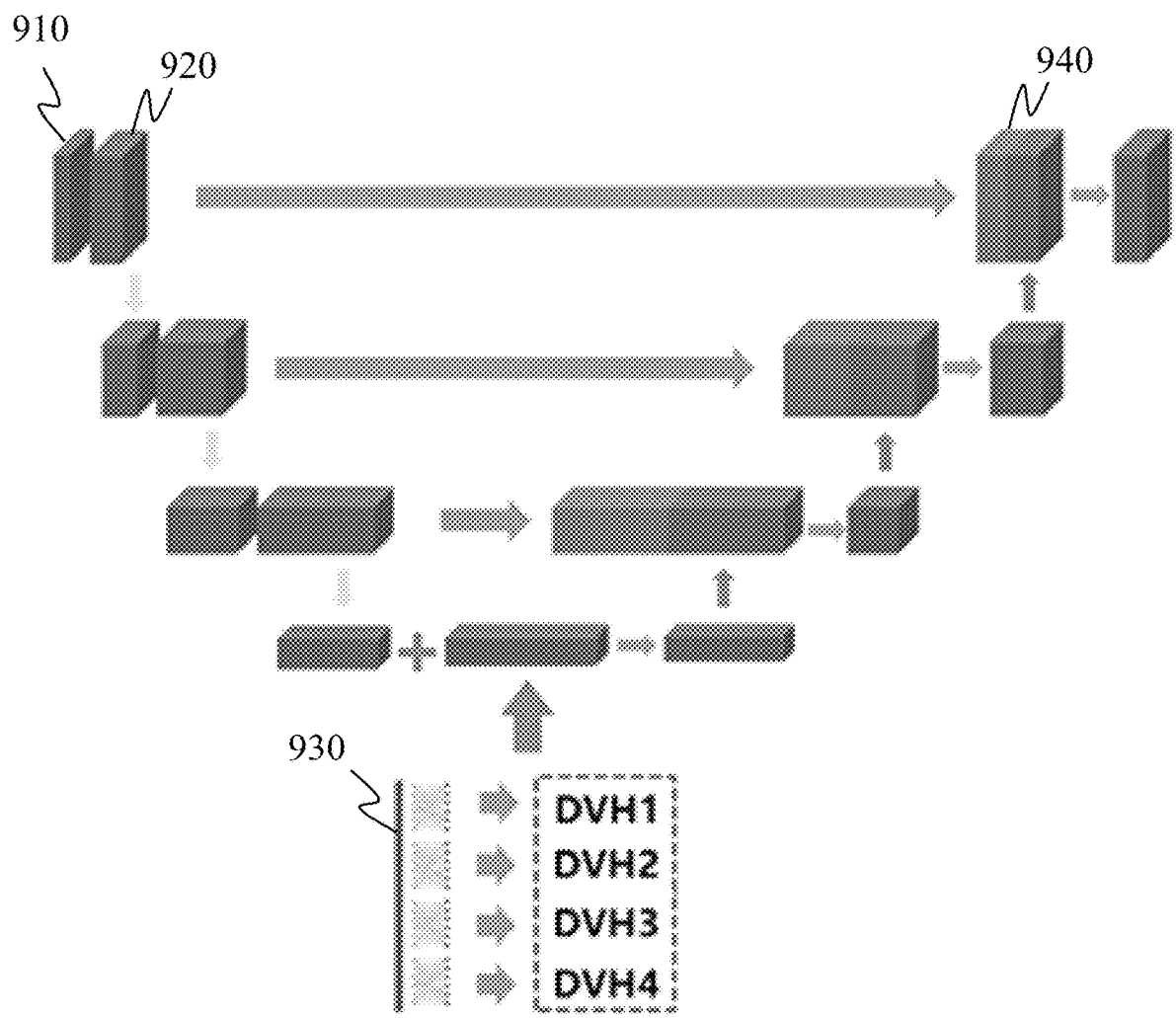
FIG. 9B is a schematic diagram illustrating an exemplary U-network for determining a dose distribution according to some embodiments of the present disclosure.

For example, as illustrated in FIG. 9B, taking a U-net network as an example, the processing device 120 may determine sample historical image data 910 and sample current image data 920 corresponding to a sample treatment fraction of a second training sample as a primary input of the U-net network, and input a sample feature parameter 930 of at least one optimization target corresponding to the sample treatment fraction into a bottom layer of the U-net network to obtain dose distribution 940 corresponding to the sample treatment fraction. The sample feature parameter 930 of the at least one optimization target corresponding to the sample treatment fraction may include DVH curves of the sample treatment fraction, such as DVH 1, DVH 2, DVH 3, and DVH 4. DVH 1 and DVH 2 may be a DVH curve of the target region and a DVH curve of the organs at risk determined based on an original treatment plan of the sample treatment fraction, and DVH 3 and DVH 4 may be a DVH curve of the target region and a DVH curve of the organs at risk set by a doctor for the sample treatment fraction.

In some embodiments, the processing device 120 may transform the sample feature parameter 930 of the at least one optimization target corresponding to the sample treatment fraction into one dimensional feature to be input into the U-net network. In some embodiments, the processing device 120 may calculate a dose feature based on the output dose distribution 940, such as a DVH curve and/or a dose feature value generated based on the output dose distribution 940. The processing device 120 may determine the value of the third loss function based on the sample feature parameter 930 corresponding to the sample treatment fraction and the dose feature, which is denoted as a consistency loss function $Loss_{consistency}$.

In 905, the processing device 120 may determine a value of a fourth loss function based on the output dose distribution and the sample dose distribution of each second training sample. In some embodiments, the fourth loss function may be denoted as a dose loss function $oss_{dose}$, which may be used to measure a difference between the output dose distribution and the sample dose distribution of each second training sample.

In 906, the processing device 120 may obtain the second dose prediction model by updating the third preliminary based on the value of the third loss function and the value of the fourth loss function.

For example, the processing device 120 may determine a value of a total loss function based on the consistency loss function and the dose loss function, for example, according to the following equation (1).

$$Loss_{total} = \lambda_1 Loss_{consistency} + \lambda_2 Loss_{dose}$$

wherein, λ1 and λ2 may be weight values determined based on an experience and/or a requirement.

In some embodiments, the processing device 120 may adjust a parameter of the third preliminary model based on the value of the total loss function to reduce the difference between the output dose distribution 940 and the sample dose distribution. For example, the value of the total loss function may be reduced or minimized by iteratively adjusting the parameter of the third preliminary model. In some embodiments, the third preliminary model may be iteratively updated based on the plurality of second training samples to make the total loss function satisfy a preset condition. For example, the total loss function may be converged or the value of the total loss function may be less than a preset value. The model training may be finished when the total loss function satisfies the preset condition. A trained third preliminary model may be determined as the second dose prediction model.

The total loss function of the third preliminary model may include the consistency loss function and the dose loss function at the same time. The dose distribution predicted by the second dose prediction model may achieve the feature parameter of the optimization target by using the consistency loss function. The dose distribution predicted by the second dose prediction model may be closer to the dose distribution in an actual usage by using the dose loss function. Accordingly, the second dose prediction model may have a higher accuracy. In addition, the input of the second dose prediction model may include the feature parameter of the first optimization target and/or the feature parameter of the second optimization target. The predicted dose distribution may better satisfy the requirements of the doctor and/or the target subject by inputting the feature parameter of the first optimization target. The predicted dose distribution may be more consistent with the original treatment plan by inputting the feature parameter of the second optimization target.

FIG. 10 is a flowchart illustrating an exemplary process 1000 for dose distribution prediction according to some embodiments of the present disclosure.

In 1010, the processing device 120 (e.g., the acquisition module 201) may obtain historical image data and current image data of a target subject.

Operation 1010 may be performed in a similar manner as operation 310, and the descriptions thereof are not repeated here.

In 1020, for each of at least one target physical point in space, the processing device 120 (e.g., the determination module 203) may determine a first sampling point corresponding to the target physical point in the historical image data and a second sampling point corresponding to the target physical point in the current image data.

The at least one target physical point may include one or more physical points on or within the target subject. In some embodiments, the at least one target physical point may include each physical point on or within the target subject. In some embodiments, the at least one target physical point may include a portion of the physical points on or within the target subject. For example, the at least one target physical point may include physical points on the target and/or the OAR of the target subject.

The first sampling point corresponding to the target physical point may be a pixel or a voxel corresponding to the target physical point in the historical image data. The second sampling point corresponding to the target physical point may be a pixel or a voxel corresponding to the target physical point in the current image data. In some embodiments, the first sampling point may be located within a first target region or a first organ at risk in the historical image data. The first target region may be a target region (e.g., PTV) in the historical image data, and the first organ at risk may be an organ at risk in the historical image data. The second sampling point may be located within a second target region or a second organ at risk in the current image data. The second target region may be a target region (e.g., PTV) in the current image data, and the second organ at risk may be an organ at risk in the current image data.

In some embodiments, the processing device 120 may determine a first sampling point in the historical image data, and determine a 3D coordinate of the target physical point corresponding to the first sampling point in space based on a coordinate of the first sampling point in an image coordinate system corresponding to the historical image data and a transformation relationship between the image coordinate system and the world coordinate system. The transformation relationship may be determined based on information relating to a radiation source, a target subject, a position relationship between detectors, or the like. In some embodiments, the historical image data and the current image data may be registered with each other to determine a first sampling point and a second sampling point that correspond to the same target physical point in space.

In 1030, for each of the at least one target physical point, the processing device 120 (e.g., the determination module 203) may determine a position difference between a first position of the first sampling point in the historical image data and a second position of the second sampling point in the current image data.

In some embodiments, for a target physical point, the first position may include a first relative position relationship between the first sampling point corresponding to the target physical point and the first target region, and the second position may include a second relative position relationship between the second sampling point corresponding to the target physical point and the second target region. The position difference may include a difference between the first relative position and the second relative position.

For example, the first sampling point may be located within a first OAR of the historical image data, and the first relative position relationship may include a minimum distance (also referred to as a first distance) from the first sampling point to the first target region. The second sampling point may be located within a second OAR of the current image data, and the second relative position relationship may include a minimum distance (also referred to as a second distance) from the second sampling point to the second target region. In some embodiments, the first distance between the first sampling point and the first target region may be determined based on a coordinate of the first sampling point in the historical image data. For example, a plurality of linear distances between the first sampling point and a plurality of sampling points on a contour line of the first target region may be determined, and a minimum linear distance may be determined as the first distance corresponding to the first sampling point. A determination of the second distance may be similar to the determination of the first distance.

In some embodiments, the first distance may be denoted as $L_1$. $L_1 > 0$ may indicate that the first sampling point is located outside the first target region, and $L_1 < 0$ may indicate that the first sampling point is located inside the first target region. The second distance may be denoted as $L_2$. $L_2 > 0$ may indicate that the second sampling point is located outside the second target region, and $L_2<0$ may indicate that the second sampling point is located inside the second target region. When the first position includes the first distance, and the second position includes the second distance, the position difference may include a first difference, which is a difference between the first distance and the second distance. In some embodiments, the position difference may be denoted as $(x, y, z, d_1)$, wherein $(x, y, z)$ indicates a 3D coordinate of the target physical point corresponding to the first sampling point and the second sampling point, and $d_1$ equals to $L_1$ minus $L_2$.

As another example, the first relative position may indicate whether the first sampling point is located within the first target region in the historical image data, and the second relative position may indicate whether the second sampling point is located within the second target region in the current image data. The position difference may include a second difference indicating whether the first relative position is consistent with the second relative position. For example, the position difference may be denoted as $(x, y, z, d_2)$. If the first sampling point is located within the first target region, and the second sampling point is located within the second target region, $d_2$ is equal to 0. If the first sampling point is not located within the first target region, and the second sampling point is not located within the second target region, $d_2$ is equal to 1. If the first sampling point is not located within the first target region, and the second sampling point is located within the second target region, $d_2$ is equal to $-1$.

As further another example, the first position may include a third relative position relationship between the first sampling point and the first OAR, and the second position may include a fourth relative position relationship between the second sampling point and the second OAR. The position difference may include a difference between the third relative position and the fourth relative position. Merely by way of example, the third relative position may indicate whether the first sampling point is located within the first OAR in the historical image data, the fourth relative position may indicate whether the second sampling point is located within the second OAR in the current image data. The position difference may include a third difference indicating whether the third relative position is consistent with the fourth relative position. For example, the position difference may be denoted as $(x, y, z, d3)$. If the first sampling point is located within the first OAR, and the second sampling point is located within the second OAR, d3 is equal to 0. If the first sampling point is not located within the first OAR, and the second sampling point is not located within the second OAR, d3 is equal to 1. If the first sampling point is not located within the first OAR, and the second sampling point is located within the second OAR, d3 is equal to $-1$.

Since the target region and/or the organs at risk may move and/or deform during a plurality of treatment fractions, the position relationship between the target physical point and the target region and the position relationship between the target physical point and the organs at risk may be changed. A change of the position relationship between the target physical point and the target region may be tracked based on the difference (i.e., the first difference and/or the second difference) between the first relative position and the second relative position. A change of the position relationship between the target physical point and the OAR may be tracked based on the difference (i.e., the third difference) between the third relative position and the fourth relative position. An accuracy of the dose prediction may be improved by considering the position relationship between the target physical point and the target region and/or the position relationship between the target physical point and the OAR, so that the predicted current dose distribution may be more applicable to the current condition of the target subject.

In some embodiments, the position difference between the first position of the first sampling point in the historical image data and the second position of the second sampling point in the current image data may be determined based on a plurality of beam eyes view (BEV) planes. A BEV plane may be a plane of the target subject perpendicular to the beam under a beam angle. A plurality of beams with different directions and/or reaching different depths may be used to irradiate the target region when the treatment is performed. Therefore, the plurality of BEV planes with different depths corresponding to different beam angles may be determined. The plurality of beam eyes view (BEV) planes may have different shapes, contours, and/or areas.

For example, for each of the BEV planes, the processing device 120 may determine a first projection position of the first sampling point and a second projection position of the second sampling point on the BEV plane, and determine a candidate difference between the first projection position and the second projection position. Merely by way of example, a candidate difference between the first projection position and the second projection position may include a difference between a relative position the first projection position to the first target on the BEV plane and a relative position the second projection position to the second target on the BEV plane, a difference between a relative position the first projection position to the first OAR on the BEV plane and a relative position the second projection position to the second OAR on the BEV plane, etc. The processing device 120 may further determine the position difference between the first position and the second position based on the candidate differences corresponding to the plurality of BEV planes. For example, for each BEV plane, a distance D1 from the first projection position to the first target on the BEV plane may be determined, a distance D2 from the second projection position to the second target on the BEV plane may be determined, and the distance difference between the distance D1 and the distance D2 may be determined as the candidate difference corresponding to the BEV plane. The processing device 120 may select the largest distance difference from the distance differences of the BEV planes, and the largest distance difference may be determined as the position difference between the first position and the second position.

Candidate difference of the BEV planes with different depths under different beam angles may be determined, and the position difference may be determined based on the candidate difference, so that a change of the target subject from the time when the historical image data is captured to the current treatment fraction may be tracked more precisely. In this way, the current dose distribution determined based on the position difference may have an improved accuracy.

In some embodiments, the position difference between the first position of the first sampling point in the historical image data and the second position of the second sampling point in the current image data may be determined based on a single BEV plane (e.g., a randomly selected BEV plane, a BEV plane with the greatest area of the target). For example, the processing device 120 may determine a first projection position of the first sampling point and a second projection position of the second sampling point on the BEV plane, and determine a difference between the first projection position and the second projection position as the position difference between the first position and the second position.

In 1040, the processing device 120 (e.g., the prediction module 202) may predict a current dose distribution to be used in the current treatment fraction based on the position difference of each target physical point using a third dose prediction model.

An input of the third dose prediction model may include the position difference of each target physical point. For example, the position difference of each target physical point may be represented as a vector (x, y, z, $d_1$, $d_2$, d3), and the vectors of the target physical points may be combined to generate a matrix. The input of the third dose prediction model may include the matrix.

In some embodiments, the input of the third dose prediction model may further include a planning dose distribution. For example, the planning dose distribution may be the dose distribution corresponding to the current treatment fraction in an original treatment plan or the dose distribution actually performed during a historical treatment fraction. Alternatively, the planning dose distribution may be determined based on the historical image data, and the planning dose distribution may correspond to the historical image data. For example, the planning dose distribution may include the dose of each second sampling point in the historical image data. As another example, the planning dose distribution may include a DVH curve of the first target region and/or a DVH curve of the first organ at risk corresponding to the historical image data. In some embodiments, the planning dose distribution may include a planning beam sub-field shape and a planning hop count. More descriptions about the planning dose distribution may be found elsewhere in the present disclosure. See, e.g., operation 410 and relevant descriptions thereof. The planning dose distribution may provide additional reference information for the third dose prediction model to determine the current dose distribution, so that the current dose distribution may be more consistent with the treatment plan and more suitable for the target subject.

In some embodiments, the output of the third dose prediction model may include the current dose distribution, for example, a dose value to be delivered to each unit volume of the target subject, the planning beam sub-field shape, the planning hop count, or the like. In some embodiments, the output of the third dose prediction model may include a difference between the current dose distribution and the planning dose distribution. The processing device 120 may determine the current dose distribution based on the planning dose distribution and the difference.

In some embodiments, the third dose prediction model may be generated by training a fourth initial model using a plurality of third training samples. For example, a sample subject may include a sample physical point, a first sampling point corresponding to the sample physical point may be identified from sample historical image data of the sample subject, and a second sampling point corresponding to the sample physical point may be identified from sample current image data of the sample subject. Each third training sample may include a sample position difference between a position of the first sampling point in the sample historical image data and a position of the second sampling point in the sample current image data. The training label corresponding to each third training sample may include sample current dose distribution used in a treatment fraction corresponding to the sample current image data of the sample subject.

FIG. 11 is a flowchart illustrating an exemplary process 1100 for dose distribution prediction according to some embodiments of the present disclosure.

In 1110, the processing device 120 (e.g., the acquisition module 201) may obtain current image data of a target subject, historical image data of the target subject, and a planning dose distribution.

Operation 1110 may be performed in a similar manner as operation 410, and the descriptions thereof are not repeated here.

In 1120, the processing device 120 (e.g., the determination module 203) may determine a plurality of candidate dose distributions based on the current image data.

A candidate dose distribution refers to dose distribution to be used in the current treatment fraction that is preliminarily determined based on the current image data. Different candidate dose distributions may correspond to different optimization styles. For example, different candidate dose distributions may have different dose features (e.g., a DVH curve, a cover ratio of the target region, an average dose received by the target region, a maximum dose received by the target region, a minimum dose received by the target region, a dose uniformity of the target region, an average dose received by the organs at risk, a maximum dose received by the organs at risk, the organs at risk requiring a special protection, or the like). Merely by way of example, a candidate dose distribution may pay more attention to delivering enough dose to the target region, while another candidate dose distribution may pay more attention to deliver less dose to the OAR.

In some embodiments, a candidate dose distribution may be determined based on the current image data and a feature parameter of at least one optimization target. For example, the at least one optimization target may relate to dose features, and the feature parameter may include a weight and/or a target value of each optimization target. An optimization objective function may be determined based on the feature parameter of the at least one optimization target, and the candidate dose distribution may be determined by solving the optimization objective function. By setting different feature parameters of the at least one optimization target, multiple candidate dose distributions corresponding to different optimization functions may be determined.

In some embodiments, the plurality of candidate dose distributions may be determined using a plurality of expert models, each of which is configured to process the current image data and determine one of the plurality of candidate dose distributions. For example, each expert model may have a specific optimization style and output candidate dose distribution with specific optimization style.

In 1130, the processing device 120 (e.g., the determination module 203) may determine a weight of each of the plurality of candidate dose distributions based on the historical image data and the planning dose distribution.

A weight of a candidate dose distribution may reflect the degree of suitability of the candidate dose distribution for the current treatment fraction. For example, a candidate dose distribution with a higher weight may be more suitable for the current treatment fraction. Since each candidate dose distribution corresponds to a specific optimization style, the weight of the candidate dose distribution may also be referred to as the weight of the optimization style corresponding to the candidate dose distribution.

In some embodiments, the weights of the candidate dose distributions may be determined by inputting the historical image data and the planning dose distribution into a gated model. The gated model may be configured to evaluate the suitability of different optimization styles (i.e., candidate dose distributions corresponding to the different optimization styles) for the current treatment fraction based on the current image data and the planning dose distribution. For example, the input of the gated model may include the current image data and the planning dose distribution, and the output of the gated model may include the weights of the different optimization styles (i.e., the weight of the candidate dose distributions).

In 1140, the processing device 120 (e.g., the prediction module 202) may predict a current dose distribution to be used in the current treatment fraction based on the plurality of candidate dose distributions and their respective weights.

For example, the current dose distribution may be a weighted sum of the candidate dose distributions determined based on the weights of the candidate dose distributions. As another example, the current dose distribution may be a candidate dose distribution that has the highest weight among the candidate dose distributions.

Figure 12:
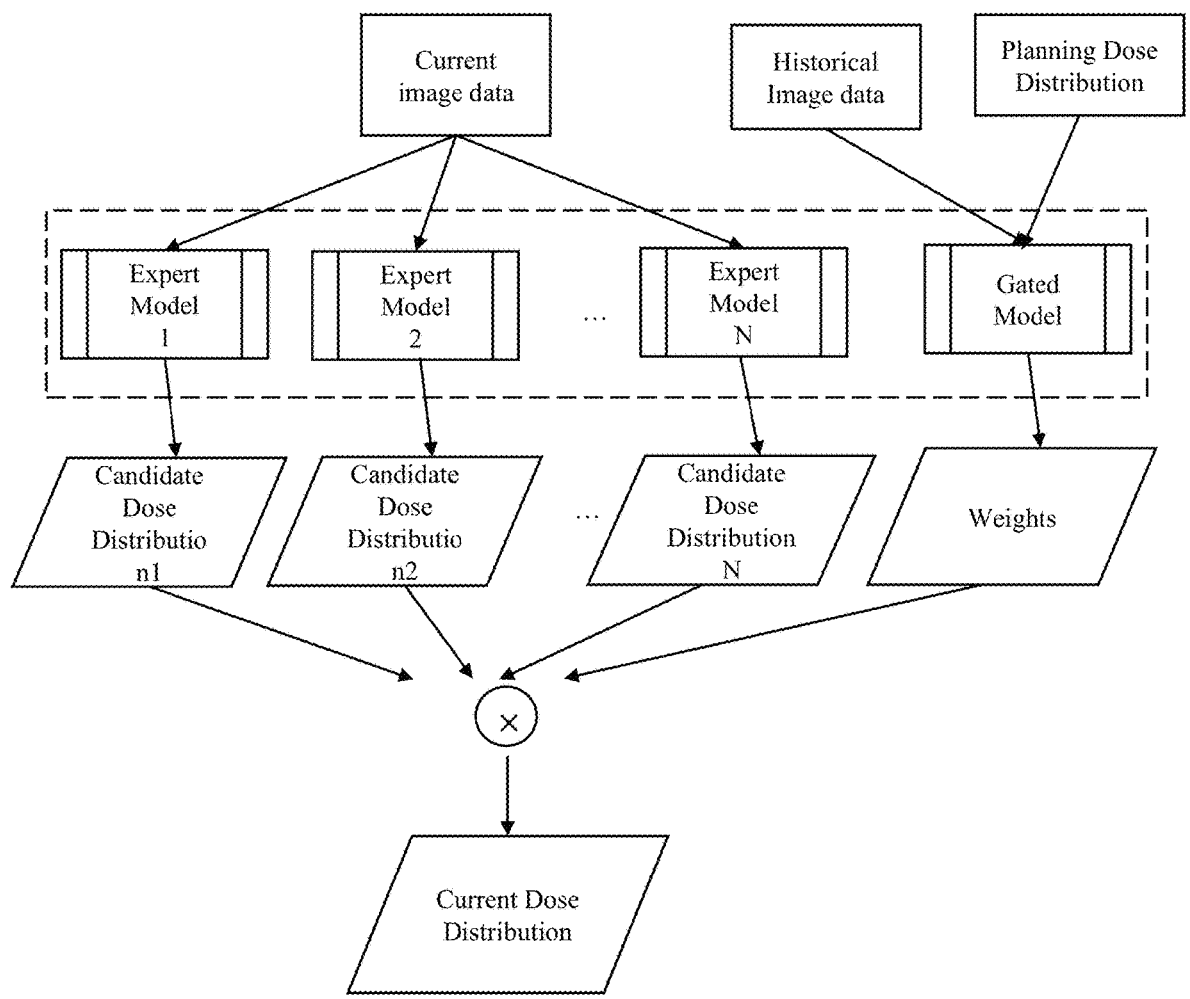
FIG. 12 is a schematic diagram illustrating an exemplary process for determining a current dose distribution according to some embodiments of the present disclosure.

For illustration purposes, FIG. 12 shows a schematic diagram illustrating an exemplary process for determining a current dose distribution according to some embodiments of the present disclosure. As illustrated in FIG. 12, an expert model 1, an expert model 2 . . . an expert model n may generate candidate dose distribution 1, candidate dose distribution 2 . . . candidate dose distribution n respectively based on the current image data. The gated model may be used to determine a weight of each candidate dose distribution based on the historical image data and the planning dose distribution. The current dose distribution may be determined based on a weighted sum of the candidate dose distributions 1-*n*.

In some embodiments, the expert models and the gated model may be components of a fourth dose prediction model. For example, the current image data, the historical image data, and the planning dose distribution may be input into the fourth dose prediction model, and the fourth dose prediction model may output the current dose distribution. Specifically, the expert models of the fourth dose prediction model may process the current image data respectively to determine the candidate dose distributions, and the gated model of the fourth dose prediction model may process the historical image data and the planning dose distribution to determine the weights of the candidate dose distributions. In some embodiments, the determination of the current dose distribution based on the candidate dose distributions and the weights may also be performed by the fourth dose prediction model.

In some embodiments, an input of the fourth dose prediction model may further include field information corresponding to the current image data and field information corresponding to the historical image data. In some embodiments, the field information may include a beam irradiation angle. The field information corresponding to the current image data may include a beam irradiation angle of a treatment plan corresponding to the current image data, and the field information corresponding to the historical image data may include a beam irradiation angle of a historical treatment plan corresponding to the historical image data. At least two expert models of the fourth dose prediction model may predict a plurality of candidate dose distributions based on the current image data and the field information of the current image data. A weighted vector may be generated by determining the historical image data, the planning dose distribution, and the field information of the historical treatment plan as the input of the gated model. The weighted vector and the plurality of candidate dose distributions may be combined to determine the current dose distribution.

According to some embodiments of the present disclosure, a plurality of expert models corresponding to different optimization styles may be used to determine candidate dose distributions corresponding to different optimization styles, so that a user does not need to select an optimization style manually, and the determined current dose distribution may combine multiple optimization styles. In addition, a gated model may be used to determine weights of the candidate dose distributions based on the historical image data and the planning dose distribution, and the current dose distribution may be determined based on the candidate dose distributions and the weights. In this way, the current dose distribution may be more consistent with the treatment plan. Both the current state of the target subject and the treatment plan are taken into consideration in dose distribution determination, thereby improving the accuracy of the determined current dose distribution.

In some embodiments, the expert models and the gated model may be jointly trained by training a fourth initial model. The fourth initial model may include a plurality of initial expert models and an initial gated model.

In some embodiments, the processing device 120 may make the plurality of initial expert models have different optimization styles by setting different initial parameters for the plurality of initial expert models. In some embodiments, the processing device 120 may determine an initial parameter of the initial gated model, so that the initial gated model may extract features of the historical image data and the planning dose distribution and predict a weight corresponding to each optimization style based on the features. That is, the optimization styles of the initial expert models may be integrated into or reflected in the initial parameter when setting the initial parameter of the initial gated model, so that the initial gated model may know the optimization styles whose weights are needed to be predicted.

FIG. 13 is a flowchart illustrating a training process 1300 of a fourth dose prediction model according to some embodiments of the present disclosure.

In 1301, the processing device 120 (e.g., the training module 204) may obtain a plurality of fourth training samples. Each fourth training sample may include sample historical image data of a sample subject, sample current image data of a sample subject, a sample planning dose distribution, and a sample dose distribution.

The sample current image data may be an image captured in a sample treatment fraction of the sample subject. The sample historical image data may be captured prior to the sample current image data. The sample planning dose distribution may be a dose distribution determined based on a treatment plan of the sample subject. The sample dose distribution may be the dose distribution performed on the sample subject during the sample treatment fraction. The sample dose distribution may correspond to the sample current image data of the sample treatment fraction. The sample dose distribution may be a label of each fourth training sample. In some embodiments, the fourth training sample may be obtained from based on historical data. For example, historical image data, current image data, a planning dose distribution, and a dose distribution corresponding to a treatment fraction performed on the sample subject may be obtained from the historical data and used as the training data.

In 1302, for each fourth training sample, the processing device 120 (e.g., the training module 204) may input the sample current image data of the fourth training sample into the initial expert models to determine a plurality of intermediate dose distributions.

The sample current image data of a fourth training sample may be input into each initial expert model to determine an intermediate dose distribution.

In 1303, for each fourth training sample, the processing device 120 (e.g., the training module 204) may input the sample historical image data and the sample planning dose distribution of the fourth training sample into the initial gated model to determine an intermediate weight of each intermediate dose distribution.

In 1304, for each fourth training sample, the processing device 120 (e.g., the training module 204) may determine an output dose distribution based on the intermediate dose distributions and their respective intermediate weights.

For example, the output dose distribution may be a weighted sum of the intermediate dose distributions determined based on the intermediate weights of the intermediate dose distributions. In some embodiments, the output dose distribution may be determined by the fourth initial model.

In 1305, the processing device 120 (e.g., the training module 204) may generate the fourth dose prediction model by updating the initial expert models and the initial gated model based on the output dose distribution and the sample dose distribution of each fourth training sample.

For example, a value of the fifth loss function may be determined based on the output dose distribution and the sample dose distribution of each fourth training sample. The fourth dose prediction model may be obtained by adjusting parameters of the at least two initial expert models and the initial gated model based on the value of the fifth loss function.

In some embodiments, the parameters of the at least two initial expert models and the initial gated model may be iteratively updated, so that the value of the fifth loss function may satisfy a preset condition. For example, the value of the fifth loss function may be converged or may be less than a preset value. The model training may be finished when the value of the fifth loss function satisfies the preset condition. The trained at least two initial expert models and the trained initial gated model may be determined as the fourth dose prediction model.

A joint training may be performed on a gated model and a plurality of expert models by training the fourth dose prediction model. Accordingly, the expert models and the gated model may be trained based on a single training set, so that the requirement on the quantity of training data may be relatively lower, thereby reducing training cost. The plurality of expert models may compete with each other, which may reduce an over-fitting effect and improve the training effect.

In some embodiments, the plurality of expert models and the gated model may be trained separately. For example, the expert models may be generated by separately training an initial expert model using different sets of training samples. Each set of training samples may correspond to one optimization style. For example, a set of training samples corresponding to a specific optimization style may include a plurality of fifth training samples, each of which includes sample current image data of a sample subject and a reference dose distribution corresponding to the specific optimization style. The reference dose distribution may be determined based on the sample current image data and a feature parameter of at least one optimization target, wherein the feature parameter may be determined based on the specific optimization style. Merely by way of example, if the specific optimization style pays more attention to protecting OARs, the weight of an optimization target relating to the dose delivered to OARs may be set higher, and a target value of the optimization target may be set lower, so that in the reference dose distribution, OARs may receive fewer radiation doses.

Each set of training samples may be used to train the initial expert model separately so that expert models corresponding to different optimization styles may be generated. In the training of the initial expert model using a set of training samples, the sample current image data of each fifth training sample in the set may be input into the initial expert model, and the initial expert model may output predicted dose distribution; and the initial expert model may be updated based on a difference between the predicted dose distribution and the reference dose distribution of each fifth training sample in the set.

The gated model may be generated based on the trained expert models. For example, the processing device 120 may obtain a plurality of sixth training samples. Each six training sample may include sample historical image data of a sample subject, a sample planning dose distribution corresponding to the sample historical image data, sample current image data of the sample subject, and a sample current dose distribution corresponding to the sample current image data. The sample current image data may be an image captured in a sample treatment fraction of the sample subject. The sample historical image data may be captured prior to the sample current image data. The sample planning dose distribution may be a dose distribution determined based on the sample historical image data (e.g., the sample historical image data may be a planning image). The sample current dose distribution may be a dose distribution used in the sample treatment fraction.

For each sixth training sample, the processing device 120 may input the sample current image data of the sixth training sample into the expert models, respectively, to determine a plurality of sample candidate dose distributions. The processing device 120 may also determine weights of the sample candidate dose distributions by processing the sample historical image data and the sample planning dose distribution of each sixth training sample using an initial gated model. Further, the processing device 120 may determine a weighted dose distribution based on the plurality of sample candidate dose distributions and their weights. The processing device 120 may then generate the gated model by updating the initial gated model based on the weighted dose distribution and the sample current dose distribution of each of the plurality of sixth training samples. For example, the initial gated model may be iteratively updated such that the difference between the weighted dose distribution and the sample current dose distribution of each six training sample is minimized.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for dose distribution prediction implemented on a computing device having at least one processor and at least one storage device, the method comprising:
   obtaining historical state information and current state information of a target subject, the current state information reflecting the state of the target subject in a current treatment fraction, and the historical state information reflecting the state of the target subject prior to the current treatment fraction;
   determining a feature parameter of at least one optimization target with respect to the current treatment fraction;
   predicting a current dose distribution to be used in the current treatment fraction based on at least part of the historical state information, the current state information, and the feature parameter of the at least one optimization target using a dose prediction model, the dose prediction model being a trained machine learning model.

2. The method of claim 1, wherein the dose prediction model includes a first dose prediction model, the determining a feature parameter of at least one optimization target with respect to the current treatment fraction comprises:
   obtaining planning dose distribution;
   determining, based on the planning dose distribution and the historical state information, the feature parameter of the at least one optimization target by using the first dose prediction model, wherein the current dose distribution is determined using the first dose prediction model based on the current state information and the feature parameter.

3. The method of claim 2, wherein
   the first dose prediction model includes a first model and a second model,
   the first model is configured to determine, based on the planning dose distribution and the historical state information, the feature parameter of the at least one optimization target, and
   the second model is configured to determine, based on the current state information and the feature parameter of the at least one optimization target, the current dose distribution.

4. The method of claim 3, wherein
   the historical state information includes historical image data of the target subject captured prior to the current treatment fraction, the determining, based on the planning dose distribution and the historical state information, feature parameter of the at least one optimization target by using the first dose prediction model comprises: determining historical anatomical information of the target subject based on the historical image data;

and determining the feature parameter of the at least one optimization target by inputting the historical anatomical information and the planning dose distribution into the first model; and the current state information includes current image data of the target subject captured in the current treatment fraction, the predicting, based on the current state information and the feature parameter of the at least one optimization target, the current dose distribution by using the dose prediction model comprises: determining current anatomical information of the target subject based on the current image data; and predicting the current dose distribution by inputting the current anatomical information and the feature parameter of the at least one optimization target into the second model.

5. The method of claim 4, wherein the predicting the current dose distribution by inputting the current anatomical information and the feature parameter of the at least one optimization target into the second model comprises:

updating, based on a difference between the current anatomical information and the historical anatomical information, the feature parameter of the at least one optimization target; and predicting the current dose distribution by inputting the current anatomical information and the one or more updated feature parameters of the at least one optimization target into the second model.

6. The method of claim 4, wherein the feature parameter of the at least one optimization target include one or more Pareto optimization parameters of the at least one optimization target.

7. The method of claim 1, wherein the at least one optimization target includes:

at least one first optimization target whose feature parameter is set by a user, and/or at least one second optimization target whose feature parameter is determined based on an original treatment plan.

8. The method of claim 1, wherein the feature parameter of the at least one optimization target includes a Dose Volume Histogram (DVH) curve of a target and/or an organ at risk (OAR) of the target subject.

9. The method of claim 1, wherein the dose prediction model includes a second dose prediction model, the second dose prediction model includes a plurality of layers, the historical state information and the current state information are input into a first layer of the plurality of layers, and the at least one optimization target is input into a second layer of the plurality of layers.

10. A method for dose distribution prediction implemented on a computing device having at least one processor and at least one storage device, the method comprising:

obtaining historical image data and current image data of a target subject, the current image data being captured before a current treatment fraction, and the historical image data being captured prior to the current image data;

for each of at least one target physical point in space,
determining a first sampling point corresponding to the target physical point in the historical image data and a second sampling point corresponding to the target physical point in the current image data; and
determining a position difference between a first position of the first sampling point in the historical image data and a second position of the second sampling point in the current image data; and predicting a current dose distribution to be used in the current treatment fraction based on the position difference of each target physical point using a dose prediction model, the dose prediction model being a trained machine learning model.

11. The method of claim 10, wherein the first position of the first sampling point in the historical image data includes a first relative position of the first sampling point to a first OAR in the historical image data, the second position of the second sampling point in the current image data includes a second relative position of the second sampling point to a second OAR in the current image data, and the position difference includes a difference between the first relative position and the second relative position.

12. The method of claim 11, wherein:

the first sampling point is located within a first OAR in the historical image data;

the first relative position includes a first distance between the first sampling point and a first target in the historical image data, the second sampling point is located within a second OAR in the current image data, the second relative position includes a second distance between the second sampling point and a second target in the current image data, and the position difference includes a difference between the first distance and the second distance.

13. The method of claim 10, wherein the first position of the first sampling point in the historical image data includes a third relative position of the first sampling point to a first target in the historical image data, the second position of the second sampling point in the current image data includes a fourth relative position of the second sampling point to a second target in the current image data, and the position difference includes a difference between the third relative position and the fourth relative position.

14. The method of claim 10, wherein the determining a position difference between a first position of the first sampling point in the historical image data and a second position of the second sampling point in the current image data comprises:

for each of a plurality of beam eye view (BEV) planes,
determining a first projection position of the first sampling point and a second projection position of the second sampling point on the BEV plane; and
determining a candidate difference between the first projection position and the second projection position; and determining, based on the candidate differences corresponding to the plurality of BEV planes, the position difference between the first position and the second position.

15. A method for dose distribution prediction implemented on a computing device having at least one processor and at least one storage device, the method comprising:

obtaining historical state information of a target subject, current state information of the target subject, and a planning dose distribution, the current state information reflecting the state of the target subject in a current treatment fraction, and the historical state information reflecting the state of the target subject prior to the current treatment fraction;

determining, based on the current state information, a plurality of candidate dose distributions;

determining, based on the historical state information and the planning dose distribution, a weight of each of the plurality of candidate dose distributions; and predicting a current dose distribution to be used in the current treatment fraction based on the plurality of candidate dose distributions and their respective weights.

16. The method of claim 15, wherein the plurality of candidate dose distributions are determined using a plurality of expert models, each of which is configured to process the current state information and determine one of the plurality of candidate dose distributions.

17. The method of claim 16, wherein the plurality of expert models are generated by jointly training a plurality of initial expert models, the plurality of initial experts models having different initial model parameters.

18. The method of claim 16, wherein the plurality of expert models are generated by separately training an initial expert model using different sets of training samples.

19. The method of claim 16, wherein the weight of each of the plurality of candidate dose distributions is determined based on the historical state information and the planning dose distribution using a gated model.

20. The method of claim 19, wherein the gated model is trained by performing a process including:

obtaining a plurality of training samples, each of which includes sample historical state information of a sample subject, a sample planning dose distribution corresponding to the sample historical state information, sample current state information of the sample subject, and a sample current dose distribution corresponding to the sample current state information;

for each of the plurality of training samples,
determining a plurality of sample candidate dose distributions by processing the sample current state information of the training sample using the plurality of expert models;
determining weights of the plurality of sample candidate dose distributions by processing the sample historical state information and the sample planning dose distribution of the training sample using an initial gated model;
determining a weighted dose distribution based on the plurality of sample candidate dose distributions and their weights;

determining the gated model by updating the initial gated model based on the weighted dose distribution and the sample current dose distribution of each of the plurality of training samples.

* * * * *